(12) United States Patent
Adelman et al.

(10) Patent No.: US 7,662,921 B2
(45) Date of Patent: Feb. 16, 2010

(54) METHODS OF TREATING VIRAL DISORDERS

(75) Inventors: Burt Adelman, Concord, MA (US); Akshay Vaishnaw, Arlington, MA (US)

(73) Assignee: Astellas US LLC, Deerfield, IL (US)

( * ) Notice: Subject to any disclaimer, the term of this patent is extended or adjusted under 35 U.S.C. 154(b) by 0 days.

(21) Appl. No.: 11/578,391

(22) PCT Filed: May 9, 2005

(86) PCT No.: PCT/US2005/016265

§ 371 (c)(1),
(2), (4) Date: Jul. 19, 2007

(87) PCT Pub. No.: WO2005/115436

PCT Pub. Date: Dec. 8, 2005

(65) Prior Publication Data

US 2008/0019960 A1   Jan. 24, 2008

Related U.S. Application Data

(60) Provisional application No. 60/568,955, filed on May 7, 2004.

(51) Int. Cl.
*C07K 14/00* (2006.01)

(52) U.S. Cl. ..................................... 530/350

(58) Field of Classification Search .............. None
See application file for complete search history.

(56) References Cited

U.S. PATENT DOCUMENTS

| | | | |
|---|---|---|---|
| 4,579,844 A | 4/1986 | Rovee et al. |
| 4,681,760 A | 7/1987 | Fathman |
| 4,738,927 A | 4/1988 | Taniguchi et al. |
| 4,816,397 A | 3/1989 | Boss et al. |
| 4,816,567 A | 3/1989 | Cabilly et al. |
| 4,833,092 A | 5/1989 | Geysen |
| 4,956,281 A | 9/1990 | Wallner et al. |
| 5,047,336 A | 9/1991 | Cate et al. |
| 5,116,964 A | 5/1992 | Capon et al. |
| 5,122,514 A | 6/1992 | Boger et al. |
| 5,185,441 A | 2/1993 | Wallner et al. |
| 5,190,859 A | 3/1993 | Dustin et al. |
| 5,225,538 A | 7/1993 | Capon et al. |
| 5,336,603 A | 8/1994 | Capon et al. |
| 5,547,853 A | 8/1996 | Wallner et al. |
| 5,556,943 A | 9/1996 | Yamashita et al. |
| 5,565,335 A | 10/1996 | Capon et al. |
| 5,728,677 A | 3/1998 | Wallner et al. |
| 5,730,979 A | 3/1998 | Bazin et al. |
| 5,817,311 A | 10/1998 | Bazin et al. |
| 5,914,111 A | 6/1999 | Wallner et al. |
| 5,928,643 A | 7/1999 | Wallner et al. |
| 5,951,983 A | 9/1999 | Bazin et al. |
| 5,952,499 A | 9/1999 | Whittaker et al. |
| 6,117,655 A | 9/2000 | Capon et al. |
| 6,162,432 A | 12/2000 | Wallner et al. |
| 6,270,766 B1 | 8/2001 | Feldman et al. |
| 6,337,337 B1 | 1/2002 | Buck |
| 6,384,198 B1 | 5/2002 | Diegel et al. |
| 6,764,681 B2 | 7/2004 | Wallner et al. |
| 2002/0009446 A1 | 1/2002 | Magilavy |
| 2003/0044406 A1 | 3/2003 | Dingivan |
| 2003/0068320 A1 | 4/2003 | Dingivan |
| 2003/0185824 A1 | 10/2003 | Vaishnow et al. |

FOREIGN PATENT DOCUMENTS

| | | |
|---|---|---|
| CA | 2120500 | 4/1993 |
| CA | 1326940 | 2/1994 |
| CA | 1338078 | 2/1996 |
| EP | 0 200 412 A2 | 12/1986 |
| EP | 0 260 880 A2 | 3/1988 |
| EP | 0 280 578 A2 | 8/1988 |
| EP | 0 314 317 B1 | 3/1989 |
| EP | 0 325 266 A2 | 7/1989 |
| EP | 0 345 466 A2 | 12/1989 |
| EP | 0 368 684 B2 | 5/1990 |
| EP | 0 50 3646 A1 | 9/1992 |
| EP | 0 503 648 A1 | 9/1992 |
| EP | 0 517 174 B1 | 12/1992 |
| EP | 0 325 262 B1 | 3/1994 |
| EP | 0 626 447 A1 | 11/1994 |
| EP | 0 607 332 B1 | 12/1997 |
| EP | 1 637 155 A1 | 3/2006 |
| JP | 63-233917 T2 | 9/1988 |
| JP | 2-501113 A2 | 4/1990 |
| JP | 1-502875 T2 | 10/1990 |
| JP | 2-503269 T2 | 10/1990 |

(Continued)

OTHER PUBLICATIONS

Glenn et al., Specific Interaction of Lymphocyte Function-associated Antigen 3 with CD2 Can Inhibit T Cell Responses, J. Exp. Med, 1993, 178:211-222.*
File history for U.S. Appl. No. 60/098,456, filed Aug. 31, 1998.
File history for U.S. Appl. No. 09/796,033, filed Feb. 27, 2001.
File history for International Application No. PCT/US99/20026, filed Aug. 31, 1999.
File history for U.S. Appl. No. 11/398,908, filed Apr. 6, 2006.
File history for U.S. Appl. No. 60/307,688, filed Jul. 24, 2001.
File history for U.S. Appl. No. 60/382,459, filed May 22, 2002.
File history for U.S. Appl. No. 10/484,329, filed Jul. 10, 2002.
File history for International Application No. PCT/US02/21631, filed Jul. 10, 2002.
File history for U.S. Appl. No. 60/568,371, filed May 4, 2004.
File history for International Application No. PCT/US05/15531, filed May 4, 2005.
File history for U.S. Appl. No. 11/578,342, filed May 4, 2005.
File history for U.S. Appl. No. 60/542,311, filed Feb. 6, 2004.
File history for International Application No. PCT/US05/03907, filed Feb. 7, 2005.

(Continued)

*Primary Examiner*—Stacy B Chen
*Assistant Examiner*—Nicole Kinsey White
(74) *Attorney, Agent, or Firm*—Leydig, Voit & Mayer, Ltd.

(57) ABSTRACT

Methods of treating viral disorders are disclosed.

1 Claim, 1 Drawing Sheet

FOREIGN PATENT DOCUMENTS

| | | |
|---|---|---|
| JP | 7-502495 T2 | 3/1995 |
| WO | WO 88/06592 A1 | 9/1988 |
| WO | WO 88/07089 A1 | 9/1988 |
| WO | WO 88/09820 A1 | 12/1988 |
| WO | WO 89/02922 A1 | 4/1989 |
| WO | WO 89/07452 A1 | 8/1989 |
| WO | WO 90/02181 A1 | 3/1990 |
| WO | WO 90/07517 A1 | 7/1990 |
| WO | WO 90/08187 A1 | 7/1990 |
| WO | WO 90/09195 A1 | 8/1990 |
| WO | WO 90/12099 A1 | 10/1990 |
| WO | WO 91/07987 A1 | 6/1991 |
| WO | WO 91/10741 A1 | 7/1991 |
| WO | WO 91/11194 A1 | 8/1991 |
| WO | WO 91/11461 A1 | 8/1991 |
| WO | WO 92/07581 A1 | 5/1992 |
| WO | WO 93/06852 A2 | 4/1993 |
| WO | WO 93/06866 A2 | 4/1993 |
| WO | WO 95/24217 A1 | 9/1995 |
| WO | WO 98/05357 A1 | 2/1998 |
| WO | WO 02/060480 A1 | 8/2002 |
| WO | WO 03/009740 A3 | 2/2003 |

OTHER PUBLICATIONS

File history for U.S. Appl. No. 10/588,323, filed Feb. 7, 2005.
File history for U.S. Appl. No. 60/568,955, filed May 7, 2004.
File history for International Application No. PCT/US05/16265, filed May 9, 2005.
File history for U.S. Appl. No. 07/667,971, filed Mar. 12, 1991.
File history for U.S. Appl. No. 07/770,967, filed Oct. 7, 1991.
File history for International Application No. PCT/US92/02050, filed Mar. 12, 1992.
File history for U.S. Appl. No. 07/940,861, filed Oct. 21, 1992.
File history for U.S. Appl. No. 08/459,512, filed Jun. 2, 1995.
File history for U.S. Appl. No. 08/459,657, filed Jun. 2, 1995.
File history for U.S. Appl. No. 08/460,132, filed Jun. 2, 1995.
File history for U.S. Appl. No. 07/772,705, filed Oct. 7, 1991.
File history for U.S. Appl. No. 07/850,706, filed Mar. 12, 1992.
File history for International Application No. PCT/US92/08754, filed Oct. 6, 1992.
File history for U.S. Appl. No. 08/211,631, filed Apr. 5, 1994.
File history for U.S. Appl. No. 08/459,350, filed Jun. 2, 1995.
File history for U.S. Appl. No. 07/770,969, filed Oct. 7, 1991.
File history for U.S. Appl. No. 07/862,022, filed Apr. 2, 1992.
File history for International Application No. PCT/US92/08755, filed Oct. 6, 1992.
File history for U.S. Appl. No. 08/466,465, filed Jun. 6, 1995.
File history for U.S. Appl. No. 09/730,465, filed Dec. 5, 2000.
File history for U.S. Appl. No. 10/778,373, filed Feb. 13, 2004.
File history for U.S. Appl. No. 11/282,853, filed Nov. 18, 2005.
File history for U.S. Appl. No. 60/265,964, filed Feb. 1, 2001.
File history for International Application No. PCT/US02/02314, filed Aug. 8, 2002.
File history for U.S. Appl. No. 10/470,764, filed Jan. 25, 2002.
File history for U.S. Appl. No. 10/329,599, filed Dec. 26, 2002.
File history for U.S. Appl. No. 11/312,627, filed Dec. 20, 2005.
File history for U.S. Appl. No. 07/057,615, filed Jun. 3, 1987.
File history for International Application No. PCT/US88/01924, filed Jun. 3, 1988.
File history for U.S. Appl. No. 07/365,107, filed Mar. 20, 1989.
File history for U.S. Appl. No. 07/537,031, filed Mar. 20, 1989.
File history for U.S. Appl. No. 08/381,299, filed Jan. 31, 1995.
File history for U.S. Appl. No. 07/237,309, filed Aug. 26, 1988.
File history for International Application No. PCT/US89/03652, filed Aug. 24, 1989.
File history for U.S. Appl. No. 07/959,550, filed Oct. 13, 1992.
File history for U.S. Appl. No. 08/261,463, filed Jun. 17, 1994 and
File history for U.S. Appl. No. 08/460,243, filed Jun. 2, 1995.
File history for U.S. Appl. No. 60/623,364, filed Oct. 28, 2004.
File history for International Application No. PCT/US05/39070.
File history for U.S. Appl. No. 11/958,917, filed Dec. 18, 2007.
Jefferis et al., IgG-Fc-medicated effector functions: molecular definition of interaction sites for effector ligands and the role of glycosylation, Immunological Reviews 1998, 163: 59-76 (Jun. 1998).
Janeway et al., Immunobiology, The immune system in health and disease, Third Edition, Current Biology Ltd./Garland Publishing Inc., New York, pp. 7:4-7:7 (1997).
United States Patent and Trademark Office, Official Communication relative to U.S. Appl. No. 10/484,329 mailed Jan. 11, 2008 (References cited on form PTO-892 are listed below).
Selman et al., Ann Intern Med. Jan. 16, 2001;134(2):136-51.
Troughton et al., Baillieres Clin Rhematol. May 1994; 8(2):439-63.
Ball et al., Angew Chem Int Ed Engl. May 3, 2005; 44(19):2852-2869.
Ziwei Huang, Pharmacol Ther. Jun. 200; 86(3):201-15.
The Merriam-Webster Online, http:www.m-w.com/cgi-bin/dictionary?interstitial as accessed on Dec. 27, 2007, 1 page. Mavilian et al., Am J. Pathol. Dec. 1997; 151(6):1751-8.
The Merck Manual of Diagnosis and Therapy, Beers et al, eds., published by Merck Research Laboratories, 17$^{th}$ ed., 1999, pp. 431-433.
Mayes et al., Environ Health Perspect. Oct. 1999; 107 Suppl 5:743-8.
Mavilia et al., Am J Pathol. Dec. 1997; 151(6): 1751-8.
Abraham et al. (1990) "Interactions between lymphocytes and dermal fibroblasts: An in vitro model of cutaneous lymphocyte trafficking," Experimental Cell Research 190, 118-126.
Abraham, et al., (1991) "Expression and Function of Surface Antigens on Scleroderma Fibroblasts" Arthritis and Rheumatism 34(9):1164-1172.
Actis, et al., "Continuously Infused Cyclosporine at Low Dose Is Sufficient to Avoid Emergency Colectomy in Acute Attacks of Ulcerative Colitis Without the Need for High-Dose Steroids", Journal of Clinical Gastroenterology, vol. 17,No. 1, pp. 10-13, 1993.
Adams, "How the Immune System Works and Why it Causes Autoimmune Diseases" Immunology Today, Jul. 1996;17(7):300-2.
Albert-Wolf, et al., "Immunomodulatory Properties of Soluble Recombinant Human CD58 (LFA-3) Molecules", Dev. Biol. Standard 77:87-92 (1992).
Alberts et al., Molecular Biology of the Cell, 1994, Garland Publishing, Inc., New York, NY, pp. 1243, 1994.
Alcover, et al., "Interdependence of CD3-Ti and CD2 Activation Pathways in Human T Lymphocytes", The EMBO Journal, vol. 7, No. 7, pp. 1973-1977, 1988.
Alora, et al., "Narrow-band (311 nm) UVB Phototherapy: An Audit of the First Year's experience at the Massachusetts General Hospital", Photodermatology Photoimmunology &Photomedicine,vol. 13, pp. 82-84, 1997.
Altman et al. (1990) "Transfection of genes for cell surface products involved in antigen presentation-applications to the understanding of autoimmunity" Autoimmunity 7:213-220.
Altmeyer, et al. "Traitement Systemique Du Psoriasis Par Les Derives De L'Acide Fumarique", Ann. Dermatol. Venereol, vol. 123, pp. 838-841, 1996.
Altshuler, "Implications of Psoriasis as a New Disease", Dermatology, vol. 199, pp. 1-2, 1999.
Ameen, "Genetic basis of psoriasis vulgaris and its pharmacogenetic potential", Pharmacogenomics 4(3); 297-308 (2003).
Arbuckle, et al., "Psoriasis" Pediatrics in Review, Mar. 1998;19(3):106-7.
Arellano, "Risk of Cancer with Cyclosporine in Psoriasis" International Journal of Dermatology, vol. 36, No. 1, pp. 15-17, 1997.
Arend, "The Pathophysiology and Treatment of Rheumatoid Arthritis" Arthritis & Rheumatism, vol. 40, No. 4, pp. 595-597, 1997.
Armitage, "Tests for Linear Trends in Proportions and Frequencies" Biometrics, 11, 375-386, 1955.
Arthos, et al., "Identification of the Residues in Human CD4 Critical for the Binding of HIV", Cell, 57(3):469-481 (1989).
Asadullah, et al., "IL-10 Is a Key Cytokine in Psoriasis", Journal of Clinical Investigation, vol. 101, No. 4, pp. 783-794, 1998.
Ashcroft, et al., "Clinical Measures of Disease Severity and Outcome in Psoriasis: A Critical Appraisal of their Quality" British Journal of Dermatology, vol. 141, pp. 185-191, 1999.
ATCC Cell Lines and Hybridomas 8th Edition 1994 p. 420 only.

Baadsgaard et al. (1989) "Psoriac Epidermal Cells Demonstrate Increased Nos. and Function of Non-Langerhans Antigen-presenting Cells" J. Invest. Dermatol. 92:190-195.
Bangha et al., "Evaluation of Topical Antipsoriatic Treatment by Chromametry, Visiometry and 20-MHz Ultrasound in the Psoriasis Plaque Test", Skin Pharmacology, vol. 9, pp. 298-306, 1996.
Bansil, et al. "Multiple Sclerosis: Immune Mechanism and Update on Current Therapies" Annals of Neurology, 37 (S1): 87-101, 1995.
Barbosa et al. (1986) "Gene Mapping and Somatic Cell Hybrid Analysis Of The Role Of Human Lymphocyte Function-Associated Antigen-3 (LFA-3) in CTL-Target Cell Interactions" J. Immunol. 136 (8):3085-3091.
Bardolph et al., "Psoriasis: A Review of Present and Future Manangement", Nursing Standard, vol. 12, No. 21, pp. 43-47, 1998.
Barker, "Psoriasis" Journal of the Royal College of Physicians of London, vol. 31, No. 3, pp. 238-240, 1997.
Barker, "The Pathophysiology of Psoriasis", The Lancet, vol. 338, pp. 227-230, 1991.
Barker, et al., "Leukocyte-Endothelium Interactions in Cutaneous Inflammatory Processes", Springer Seminars in Immunopathology, vol. 13, pp. 355-367, 1992.
Barker, et al., "Topical Maxacalcitol for the Treatment of Psoriasis Vulgaris: A Placebo-Controlled, Double-Blind, Dose-Finding Study with Active Comparator", British Journal of Dermatology, vol. 141, pp. 274-278, 1999.
Barsoum, "Introduction of Stable High-Copy-Number DNA into Chinese Hamster Ovary Cells by Electroporation" DNA and Cell Biology, vol. 9, No. 4, pp. 293-300, 1990.
Barthels et al., "Isolation and Nucleotide Sequence of Mouse NCAM cDNA that Codes for a M.sub.r 79000 Polypeptide Without a Membrane-Spanning Region," EMBO Journal, 6 (4), pp. 907-914 (1987).
Bay, et al., "Psoriasis Patients have T-cells with Reduced Responsiveness to Common Mycobacterial Antigens", FEMS Immunology and Medical Microbiology, vol. 21, pp. 65-70, 1998.
Bell, et al, "CD2 and the Regulation of T Cell Anergy", J Immunol. Sep. 15, 1995;155(6):2805-7.
Benjamin, et al., "MAb to cell interaction antigens block human T-dependent B cell activation", J. Cell. Biochem. Keystone Symposia on Molecular & Cellular Biology Supp. 17B:172 (1993).
Bennet, "Cyclosporine Nephrotoxicity: Implications for Dermatology", International Journal of Dermatology, vol. 36(Supp. 1), pp. 11-14, 1997.
Benton et al., "Screening the Recombinant Clones by Hybridization to Single Plaques in situ", Science, 196, 180-182 (1977).
Berth-Jones, et al., "Treatment of Psoriasis with Intermittent Short Course Cyclosporin (Neoral.RTM.). A Multicentre Study", British Journal of Dermatology, vol. 136, pp. 527-530, 1997.
Bieber et al. (1981) "Complications in long-term survivors of cardiac transplantation", Transplant Proc. 8(1): 207-211.
Bierer, et al. (1988) "T Cell Adhesion Molecules" FASEB J. 2:2584-2590.
Bierer et al. (1988) "Expression Of The T-Cell Surface Molecule CD2 And An Epitope-Loss CD2 Mutant To Define The Role Of Lymphocyte Function-Associated Antigen 3 (LFA-3) in T-Cell Activation" Proc. Natl. Acad. Sci. USA 85:1194-1198.
Bierer et al. (1989) "A Monoclonal Antibody to LFA-3, the CD2 Ligand, Specifically Immobilizes Major Histocompatibility Complex Proteins" Eur. J. Immunol. 19:661-665.
Bierer, B. et al. "Synergistic T cell activiation via the physiological ligands for CD2 and the T cell receptor", J. Exp. Med. 168:1145-1156, Sep. 1988.
Bjerke, et al., "Acitretin Versus Etretinate in Severe Psoriasis. A double-blind Randomized Nordic Multicenter Study in 168 Patients", Acta Derm Venereol Suppl (Stockh), Vool. 146, pp. 206-207, 1989.
Bjerring, et al., "Topical Treatment of Psoriatic Skin with Methotrexate Cream: A Clinical, Pharmacokinetic, and Histological Study", Acta Derm Venereol (Stockh), vol. 66, pp. 515-519, 1986.
Bockenstedt et al. (1988) "The CD2 Ligand LFA-3 Activates T Cells But Depends On The Expression And Function Of The Antigen Receptor" J. Immunol. 141:1904-1911.

Boehncke, et al., "Differential Expression of Adhesion Molecules on Infiltrating Cells Inflammatory Dermatoses", Journal of American Academy of Dermatology, vol. 26, No. 6, pp. 907-913, 1992.
Bonifati, et al., "Recognition and Treatment of Psoriasis: Special Considerations in Elderly Patients" Drugs & Aging, vol. 12, No. 3, pp. 177-190, 1998.
Bonnerjea, et al. "Protein Purification: The Right Step at the Right Time" Bio/Technology 4:955 (1986).
Borroni, et al., "Evidence for CD8+ Cell Increase in Long-Term PUVA-Treated Psoriatic Patients after PUVA Discontinuation", Dermatology, vol. 185, pp. 69-71, 1992.
Bos, et al., "Immunologie in de Medische Praktijk. VII. Psoriasis", Ned Tijdschr Geneeskd, vol. 141, No. 48, pp. 2334-2338, 1997.
Bouhnik, et al., "Long- term Follow-up of Patients with Crohn's Disease Treated with Azathioprine or 6-Mercaptopurine", The Lancet, vol. 347, pp. 215-219, 1996.
Bovenschen, et al., "Explorative immunohistochemical study to evaluate the addition of a topical corticosteroid in the early phase of alefacept treatment for psoriasis", Arch. Dermatol. Res. 298: 457-463 (2007).
Bowie et al. Deciphering the messages in protein sequences: Tolerance to amini acid substitutions. Science 240:1306-1310, Mar. 1990.
Bressler, P., et al., "Anti-CD2 Receptor Antibodies Activate the HIV Long Terminal Repeat in T Lymphocytes," J. Immunol., 147(7), pp. 2290-2294 (Oct. 1, 1991).
Brod, S. A. et al., "T-T Cell Interactions Are Mediated by Adhesion Molecules," Eur. J. Immunol., 20, pp. 2259-2268 (1990).
Bromberg et al. (1991) "Anti-CD2 Monoclonal Antibodies Alter Cell-Mediated Immunity In Vivo" Transplantation 51:219-225.
Brottier, et al., "T Cell Activation Via CD2 [T, gp50] Molecules: Accessory Cells are Required to Trigger T Cell Activation via CD2-D66 Plus CD2-9.6/T11.sub.I Epitopes.sup.I ", The Journal of Immunology, vol. 135(3), pp. 1624-1631, 1985.
Brown et al. (1987) "T2.2 Characterization of CD2 Epitopes By Western Blotting" in Leukocyte Typing III, A.J. McMichael (ed.) Oxford, England: Oxford University Press, 110-112.
Brown et al. (1989) "The CD2 Antigen Associates With The T-Cell Antigen Receptor CD3 Antigen Complex On The Surface of Human T Lymphocytes" Nature 339: 551-553.
Bucherri, et al., "Acitretin Therapy is Effective for Psoriasis Associated with Human Immunodeficiency Virus Infection", Archives of Dermatology, vol. 133, pp. 711-715, 1997.
Burden, "Management of Psoriasis in Childhood", Clinical and Experimental Dermatology, vol. 24, pp. 341-345;1999.
Burns, et al., "Intralesional Cyclosporine for Psoriasis", Archives of Dermatology, vol. 128, pp. 786-790, 1992.
Camisa, Psoriasis, Blackwell Scientific Publications, 1994, 1.sup.st Ed.
Capon, et al., "Designing CD4 immunoadhesins for AIDS therapy", Nature 337(9): 525-531(1989).
Carrera, et al. "Triggering of co-mitogenic signals in T cell proliferations by anti-LFA-1 (CD18, CD11a), CLA-3, and CD7 monoclonal antibodies", J. Immunol. 141(6):1919-1924 (1988).
Cate, et al., "Isolation of the Bovine and Human Genes for Mullerian Inhibiting Substance and Expression of the Human Gene in Animal Cells", Cell, 45, 685-698 (1986).
Cerdan, et al., "Prolonged IL-2 receptor α/CD25 expression after T cell activation via the adhesion molecules CD2 and CD28", J. Immunol. 149(7):2255-2261 (1992).
Chandraratna, "Tazarotene: The First Receptor-Selective Topical Retinoid for the Treatment of Psoriasis", American Academy of Dermatology, vol. 37, No. 2, pp. S12-S17, 1997.
Chang et al. (1992) "T-Cell Activation Is Potentiated by Cytokines Released by Lesional Psoriatic, but Not Normal, Epidermis" Arch. Dermatol. 128:1479-1785.
Chavin, et al., "Prolongation of allograft and xenograft survival in mice by anti-CD2 monoclonal antibodies", Transplantation, 54(2):286-291 (1992).
Chin, Y.H. et al. "Lymphocyte Recognition of Psoriatic Endothelium: Evidence for a Tissue-Specific Receptor/Ligand Interaction",J. Invest. Dermatol. 93(2) Supplemental: 82S-87S (1989).

Chisholm et al. (1994) "The effects of an immunodulatory LFA3-IgG.sub.1 fusion protein on nonhuman primates," Therapeutic Immunology 1: 205-216.

Christiansen, et al., "Etretinate (Tigason.RTM.) and Betamethasone Valerate (Celeston Valerate.RTM.) in the Treatment of Psoriasis", Dermatologica, vol. 165, pp. 204-207, 1982.

Christophers, et al., "The Inflammatory Infiltrate in Psoriasis", Clinics in Dermatology, vol. 13, pp. 131-135, 1995.

Christophers, et al., "Cyclosporine in Psoriasis: A Multicenter Dose-Finding Study in Severe Plaque Psoriasis", Therapy, Journal of the American Academy of Dermatology, vol. 26, No. 1, pp. 876-890, 1992.

Church, et al., "Genomic Sequencing", Proc. Natl. Acad. Sci. U.S.A., 81, 1991-1995 (1984).

Clayton et al. (1987) "Murine and Human T11 (CD2) cDNA Sequences Suggest A Common Signal Transduction Mechanism" Eur. J. Immunol. 17: 1367-1370.

Cohen, et al., "Immunomodulatory Agents and Other Medical Therapies in Inflammatory Bowel Disease" Current Opinion in Gastroenetrology, vol. 11, pp. 321-330, 1995.

Colten, "Pulmonary Inflammation-A Balancing Act", N Engl J Med. Apr. 10, 1997;336(15):1094-6.

Colvin, et al., "Cellular and Molecular Mechanisms of Allograft Rejection", Ann Rev Med 41:361-375 (1990).

Conti et al., (1990) "Effect of Monoclonal Antibodies on Primate Allograft Rejection" Crit. Rev. Immunol. 10(2): 113-130.

Conzelmann et al. (1986) "Anchoring of membrane proteins via phosphatidylinositol is deficient in two classes of Thy-1 negative mutant lymphoma cells", The EMBO J., vol. 5, No. 12, pp. 3291-3296.

Cooper (1990) "Immunoregulation in the Skin" Current Problems in Dermatology 19:69-80.

Cooper (1992) "Skin-infiltrating Lymphocytes in Normal and Disordered Skin: Activation Signals and Functional Roles in Psoriasis and Mycosis Fungoides-types Cutaneous T Cell Lymphoma" J. Dermatol. 19:731-737.

Cooper et al. (1985) "Effects of ultraviolet radiation on human epidermal cell alloantigen presentation: initial depression of langerhans cell-dependent function is followed by appearance of T6-Dr+ cells that enhance epidermal alloantigen presentation" J. Immunol. 134(1):129-137.

Cosimi et al.; "In Vivo Effects of Monoclonal Antibody to ICAM-1 (CD54) in Nonhuman Primates with Renal Allografts.sup.1" (The Journal of Immunology—Jun. 15, 1990 pp. 4604-4612).

Cosomi et al.; "Prolonged survival of nonhuman primate renal allograft recipients treated only with anti-CD4 monoclonal antibody" Surgery, 108 (2): 1990 pp. 406-414).

Cosimi, et al. "Immunosuppression of Cynomolgus Recipients of Renal Allografts . . . " Leukocyte Adhesion Molecules (Springer-Verlog 1988) pp. 275-281.

Cosimi, et al., "Anti-T-Cell Monoclonal Antibodies in Transplantation Therapy", Transplantation Proc. 15(3):1889-1892 (1983).

Crispe, and Mehal, "Strange Brew: T Cells in the Liver"Immunology Today, vol. 17, No. 11, pp. 522-525, 1996.

Cronstein, "The Mechanism of Action of Methotrexate", Rheumatic Disease Clinics of North America, vol. 23, No. 4, pp. 739-755, 1997.

Cuelar, et al., "Psoriatic Arthritis Current Developments" J. Florida M.A. 82(5):338-342 (1995).

Cunningham and Harris (1992) "Antibody engineering—how to be human" TIBTECH 10.

Cunningham et al., "Neural Cell Adhesion Molecule: Structure, Immunoglobulin-Like Domains, Cell Surface Modulation, and Alternative RNA Splicing," Science, 236, pp. 799-806 (1987).

Curtis, et al. (1992) "The Nature of Science" in Biology, 5.sup.th ed. (Worth Publishers, Inc.): 14-15.

Dailey, et al., "Sequences in the Polyomavirus DNA Regulatory Region Involved in Viral DNA Replication and Early Gene Expression," J. Virology, 54 (3), pp. 739-749 (Jun. 1985).

Damle, et al., "Costimulation of T lymphocytes with integrin ligands inttercellular adhesion molecule 1 or vascular cell adhesion molecule 1 induces functional expression of CTLA-4, a second receptor for B7" J. Immunol (1994).

Damle, et al., "Stimulation of cloned human T lympocytes via the CD3 or CD28 molecules induces enhancement in vascular endothelial permability to macromolecules with participation of type -1 and type-2 intercellular adhesion pathways" Eur. J. Immunol. 20 (9):1995-2003 (1990).

Damle, N., et al., "Differential Costimulatory Effects of Adhesion Molecules B7, ICAM-1, LFA-3, and VCAM-1 on Resting and Antigen-Primed CD4.sup.+ T Lymphocytes" The Journal of Immunology, vol. 148, 1985-1992, No. 7 (Apr. 1, 1992);.

Danielian, et al., "The Tyrosine Kinase Activity of p56.sup.kk is Increased in Human T Cells Activated via CD2", European Journal of Immunology, vol. 21, pp. 1967-1970, 1991.

Davies, and Morris, "Physiological Parameters in Laboratory Animals and Humans" Pharmaceutical Research, vol. 10, No. 7, pp. 1093-1095, 1993.

Dawe, et al., "Narrow-Band (TL-01) Ultraviolet B Phototherapy for Chronic Plaque Psoriasis: Three Times of Five Times Weekly Tratment?" British Journal of Dermatology, vol. 1, No. 38, pp. 833-839, 1998.

Deckert, et al., "CD59 molecule: A second ligand for CD2 in T cell adhesion", Eur. J. Immunol. 22:2943-2947 (1992).

Denning et al. (1987) "Monoclonal Antibodies to CD2 and Lymphocyte Function-Associated Antigen 3 Inhibit Human Thymic Epithelial Cell-Dependent Mature Thymocyte Activation" J. Immunol. 139(8):2573-2578.

Denning et al. (1988) "Purified Lymphocyte Function-Associated Antigen-3 (LFA-3) Activates Human Thymocytes Via The CD2 Pathway" J. Immunol. 141(9): 2980-2985.

Dente, L., et al., "pEMBL: a New Family of Single Stranded Plasmids," Nucleic Acids Research, 11(6), pp. 1645-1655 (1983).

Department of Health & Human Services, "International Conference on Harmonisation" Federal Register, vol. 62, No. 222, pp. 61515-61519, 1997.

Ding et al. (1996) "A novel murine model for the assessment of human CD2-related reagents In Vivo," J. Immunol. 157(5): 1863-1869.

Dinowitz, et al., "Recent Studies on Retrovirus-Like Particles in Chinese Hamster Ovary Cells", Developments in Biological Standardizations, vol. 76, pp. 201-207, 1991.

Drake, et al., "Guidelines of Care for Psoriasis", Journal of American Academy of Dermatology, vol. 28, No. 4, pp. 632-637, 1993.

Driscoll, et al., "Structure of Domain 1 of Rat T Lymphocyte CD2 Antigen", Nature, vol. 353, pp. 762-765, 1991.

Dustin et al. (1987) "Purified Lymphocyte Function-Associated Antigen 3 Binds to CD2 And Mediates T Lymphocyte Adhesion" J. Exp. Med. 165(3): 677-692.

Dustin et al. (1987) "T Cell Activation By LFA-3 and CD2 Antibodies" FASEB J. 45:A1239 (Abstract No. 5484).

Dustin, and Springer, "Role of Lymphocyte Adhesion Receptors in Transient Interaction and Cell Locomotion" Annual Review of Immunology, vol. 9, pp. 27-66, 1991.

Dustin, and Springer, "T-Cell Receptor Cross-Linking Transiently Stimulates Adhesiveness Through LFA-1" Nature, vol. 341, pp. 619-624, 1989.

Dustin, et al., "Anchoring Mechanisms for LFA-3 Cell Adhesion Glycoprotein at Membrane Surface", Nature, vol. 329, 846-848, 1987.

Dustin, et al., "Low Affinity Interaction of Human or Rat T Cell Adhesion Molecule CD2 with Its Ligand Aligns Adhering Membranes to Achieve High Physiological Affinity", The Journal of Biological Chemistry vol. 272, No. 49, pp. 30889-30898,1997.

Dustin, M. L., et al., "Correlation of CD2 Binding and Functional Properties of Multimeric and Monomeric Lymphocyte Function-Associated Antigen 3," J. Exp. Med., 169, pp. 503-517 (Feb. 1989).

Duvic, et al., "Molecular Mechanisms of Tazarotene Action in Psoriasis", Journal of American Academy of Dermatology, vol. 37, No. 2, pp. S18-S24, 1997.

Economidou, et al., "Effects of Cyclosporin A on Immune Activation Markers in Patients with Active Psoriasis", Dermatology, vol. 199, pp. 144-148, 1999.

Edelhoch, "Spectroscopic Determination of Tryptophan and Tyrosine in Proteins" Biochemistry, vol. 6, No. 7, pp. 1948-1954, 1967.

Ehmann, and Voorhees, "Effect of Oral Synthetic Retinoids on Keratinizing Disorders", Journal of American Academy of Dermatology, vol. 6, No. 4, pp. 692-696, 1982.

Ekborn, et al., "Crohn's Disease After In-Utero Measles Virus Exposure", The Lancet, vol. 348, pp. 515-517, 1996.

Elder, et al., "Efficacy and Pharmacokinetics of Two Formulations of Cyclosporine A in Patients with Psoriasis" Journal of Clinical Pharmacology, vol. 35, pp. 865-875, 1995.

Ellis, "Quality of Life Results from a Randomized Double Blind Multi Center Dose Response study of LFA3TIP in patients with Chronic Plaque Psoriasis" Am Acad Dermatol. 58th Ann Meeting Mar. 10-15, 2000. (Abstract).

Ellis, et al., "Cyclosporine for Plaque-Type Psorisis: Results of a Multidose, Double-Blind Trial", The New England Journal of Medicine vol. 324, No. 5, pp. 276-284, 1991.

Ellis, et al., "Treatment of chronic plaque psoriasis by selective targeting of memory effector T lymphocytes", The New England J. Med. 345(4):248-255 (2001).

Enea, V. and N. D. Zinder, "Interference Resistant Mutants of Phage f1," Virology, 122, pp. 222-226 (1982).

Ewe, et al., "Azathioprine and Prednisolone for Active Crohn Disease", ACP Journal Club, 1994, Annals of Internal Medicine 120/2 Suppl. 1 (13).

Ezekowitz, et al., "The Interferons: Basic Biology and Therapeutic Potential" in Therapeutic Immunology, edited by Austen et al., (Blackwell Science, Cambridge, MA, 1996) 249-263.

Farber, "Juvenile Psoriasis: Early Interventions Can Reduce Risks for Problems Later" Postgraduate Medicine vol. 103, No. 4, pp. 89-100, 1998.

Farber, et al. "Psoriasis: A Disease of the Total Skin" Journal of American Academy of Dermatology, vol. 12(1), pp. 150-156, 1985.

Faulds, et al., "Cyclosporin: A Review of its Pharmacodynamic and Pharmacokinetic Properties, and Therapeutic Use in Immunoregulatory Disorders", Drugs, vol. 45, No. 6, pp. 953-1040, 1993.

Feagan, et al., "Methotrexate for the Treatment of Crohn's Disease" The New England Journal of Medicine, vol. 332(5), pp. 292-297, 1995.

Feagan, et al., "Methotrexate Improved Symptoms in Chronic Active Crohn Disease", ACP Journal Club, Jul.-Aug. 1995;123(1) 9.

Feagan, et al., "Therapeutics and Inflammatory Bowel Disease: A Guide to the Interpretation of Randomized Controlled Trials" Gastroenterology, vol. 110, pp. 275-283, 1996.

Feldman, et al., "The Economic Impact of Psoriasis Increases with Psoriasis Severity" Journal of American Academy of Dermatology, vol. 37(4), pp. 564-569, 1997.

Feldman, et al., "The Self-Administered Psoriasis Area and Severity Index Is Valid and Reliable", Journal of Investigative Dermatology, vol. 106, pp. 183-186, 1996.

Ferguson et al. (1988) "Cell-surface anchoring of proteins via glycosyl-phosphatidylinositol structures", Ann. Rev. Biochem., vol. 57, pp. 285-320.

Feracilli, et al., "Effects of cyclosporine on joint damage in rheumatoid arthritis", Clin Exp. Rheum. 15 (Supp 17):S83-S89 (1997).

Ffrench-Constant, "Pathogenesis of Multiple Sclerosis", The Lancet, vol. 343, pp. 272-278, 1994.

Findlay "Purification of Membrane Proteins" Ch. 4 in Protein Purification Applications, A Practical Approach (Harris and Angel, eds) 1990 (cited for argument).

Findlay, and Khan, "Dermatology Life Quality Index (DLQI): A Simple Practical Measure for Routine Clinical Use", Clinical and Experimental Dermatology, vol. 19, pp. 210-216, 1993.

Finzi, et al., "A Clinical Survey of Psoriasis in Italy: 1.sub.st AISP Report" Journal of the European Academy of Dermatology and Venereology, vol. 10,pp. 125-129, 1998.

Finzi, et al., "Cyclosporin versus Etretinate: Italian Multicenter Comparative Trial in Severe Plaque-Form Psoriasis", Dermatology, vol. 187(suppl 1), pp. 8-18, 1993.

First, "Transplantation in the Nineties", Transplantation 53(1):1-11 (1992).

Fishel, et al. "The cellular response to xenotransplantation", Curr. Surg. 47(5):345-347 (1990).

Fisher, "T cell adhesion", J. Exp. Clin. Hematol. 32:49-51 (1990).

Fleischer, Jr., et al., "Disease Severity Measures in a Population of Psoriasis Patients: The Symptoms of Psoriasis Correlate with Self-Administered Psorisis Area Severity Index Scores", Journal of Investigative Dermatology, vol. 107, No. 1, pp. 26-29, 1996.

Fleischer, Jr., et al., "Patient Measurement of Psoriasis Disease Severity with a Structured Instrument" Journal of Investigative Dermatology, vol. 102, No. 6, pp. 967-969, 1994.

Fortune, et al., "Quality of Life in Patient with Psoriasis: the Contribution of Clinical Variables and Psoriasis-Specific Stress", British Journal of Dermatology, vol. 137, pp. 755-760, 1997.

Fox, "The Role of T Cells in the Immunopathogenesis of Rheumatoid Arthritis", Arthritis & Rheumatism, vol. 40, No. 4, pp. 598-609, 1997.

Gamache et al. (1996) "Pharmacokinetics of LFA3TIP, an immunoglobulin fusion protein, in male and female baboons," Pharmaceutical Research 13 (9 Sup.): s399 (Abstract).

Gasgoigne et al., "Secretion of a chimeric T-cell receptor-immunoglobulin protein", 1987, P.N.A.S. USA, vol. 84;2936-2940.

Geider, K., et al., "A Plasmid Cloning System Utilizing Replication and Packaging Functions of the Filamentous Bacteriophage fd," Gene, 33, pp. 340-349 (1985).

Genmab Press release 48/2002 "HuMAX CD-4 in combination therapy not effective in Rheumatoid Arthritis".

Georgouras, et al. "Systemic Treatment of Severe Psoriasis", Australasian Journal of Dermatology, vol. 38, pp. 171-182, 1997.

Gimenez-Arnau, et al., "Psoriasis: bases de actuacion terapeutica", Act. Dermatolog.3:159-171(1998).

Giorgi, et al, "Immunosuppressive Effect and Immunogenicity of OKT11A monoclonal antibody in monkey allograft recipients", Transplantation Proc. 15(1):639-642 (1983).

Gismondi, et al., "Triggering through CD16 or Phorbol Esters Enhances Adhesion of NK Cells to Laminin via Very Late Antigen 6", Journal of Experimental Medicine, vol. 176,pp. 1251-1257,1992.

Goebel, et al., "Drug Trials in Inflammatory Bowel Diseases 1993-1995: A Survey Conducted by the IOIBD", Inflammatory Bowel Diseases, vol. 2, pp. 265-267, 1996.

Goedkoop et al., "Alefacept therapy reduces the effector T-cell population in lesional psoriatic epidermis", Arch. Dermatol. Res. 295:465-473 (2004).

Goldman, et al., "OKT3-Induced Cytokine Release Attenuation by High-Dose MethilPrednisolone", Lancet. Sep. 30, 1989;2(8666):802-3.

Gollnick, et al., "Acitretin* versus Etretinate in Psoriasis: Clinical and Pharmacokinetic Results of a German Multicenter Study", Journal of American Academy of Dermatology, vol. 19, No. 3, pp. 458-468, 1988.

Gollob, et al., "CD2 Regulates Responsivenes of Activated T Cells to Interleukin 12", Journal of Experimental Medicine, vol. 182, pp. 721-731, 1995.

Gonzales-Ramos et al. (1992) "APC-Targeted Immunointervention in Psoriasis: Blockade of LFA-3-CD2 and ICAM 1-LFAI Ligand Pairing Blocks Autoreactivity to Lesional Epidermis" Clinical Research 40(2):500A.

Gordon, et al., "Treatment of psoriasis with alefacept", Arch. Dermatol. 139: 1563-1570 (2003).

Gottlieb, "The Challenges of Treating Moderate to Severe Psoriasis", International Journal of Dermatology, vol. 36(suppl 1), pp. 41-44, 1997.

Greaves, and Weinstein, "Treatment of Psorisis", The New England Journal of Medicine, vol. 332, No. 9, pp. 581-588, 1995.

Greenberg, et al., "Oral Budesonide for Active Chrohn's Disease", The New England Journal of Medicine, vol. 331, No. 13, pp. 836-845, 1994.

Gregersen, et al., "A CD4: immunoglobulin fusion protein with antiviral effects against HIV", Arch. Virol. 111:29-43 (1990).

Grossman, et al., "A Novel Therapeutic Approach to Psoriasis with Combination Calcipotriol Ointment and Very-Low-Dose Cyclosporine: Results of a Multicenter Placebo-Controlled Study", Journal of American Academy of Dermatology, vol. 31, No. 1, pp. 68-74, 1994.

Grossman et al., "Long-term Safety of Cyclosporine in the Treatment of Psoriasis", Archives of Dermatology, vol. 132, pp. 623-629, 1996.

Grosveld, et al., "The Construction of Cosmid Libraries Which Can Be Used to Transform Eukaryotic Cells", Nucl. Acids. Res., 10(21), 6715-6732 (1982).

Gubler, et al., "A Simple and Very Efficient Method for Generating cDNA Libraries", Gene, 25, 263-269 (1983).

Guckian, et all., "Immunomodulation at the Initiation of Phototherapy and photochemotherapy", Photodermatology, Photoimmunology & Photomedicine, vol. 11, pp. 163-169, 1995.

Gulliver, et al., Increased Bioavailability and Improved Efficacy, in Severe Psoriasis, of a New Microemulsion Formulation of Cyclosporin*, British Journal of Dermatology, vol. 135(suppl 48), pp. 35-39, 1996.

Guzzo, "Recent Advances in the Treatment of Psoriasis", Dermatologic Clinics, vol. 15, No. 1, pp. 59-68, 1997.

Hafler, et al., "Anti-CD4 and anti-CD2 monoclonal antibody infusions in subjects with multiple sclerosis", J. Immunol. 141(1):131-138 (1988).

Hale, et al. "Bromelain treatment of human T cells removes CD44, CD45RA, E2/MIC2, CD6, CD7, CD8, and Leu 8/LAM1 surface molecules and markedly enhances CD2-mediated T cell activation", J. Immunol. 149(12):3809-3816 (1992).

Hamblin, "From Dendritic Cells to Tumour Vaccines", The Lancet, vol. 347, pp. 705-706, 1996.

Hanauer, "Inflammatory Bowel Disease", Drug Therapy, vol. 334, No. 13, pp. 841-848,1996.

Hanauer, "Medical Therapy of Ulcerative Colitis"The Lancet, vol. 342, pp. 412-417, 1993.

Hardman, et al., "Active Psoriasis and Profound $CD4^+$ Lymphocytopenia", British Journal Of Dermatology, vol. 136, pp. 930-932, 1997.

Harris and Emery (1993) "Therapeutic antibodies—the coming of age" TIBTECH 11: 42-44.

Hawke, et al., "Autoimune T Cells in Myasthenia Gravis: Heterogeneity and Potential for Specific Immunotargeting", Immunology Today, vol. 17, No. 7, pp. 307-311, 1996.

Hawkes, et al., "A Dot-Immunobinding Assay for Monoclonal and Other Antibodies", Anal. Biochem., 119, 142-147 (1982).

Haynes, B.F. et al. "Synovial microenvironment-T cell interactions", Arthritis and Rheum. 31 (8): 947-955 (1988).

He et al., "Phosphatidylinositol is Involved in the Membrane Attachment of NCAM-120, the Smallest Component of the Neural Cell Adhesion Molecule," EMBO Journal, 5, (10), pp. 2489-2494 (1986).

Hebel, et al., "Suppression of the immune response by a soluble complement receptor of B lymphocytes", Science 254(5028):102-105 (1991) (cited for argument).

Heij (La Heij), et al., "Adhesion molecules in iris biopsy specimens from patients with uveitis", Br. J. Opthamol. 82(4):432-437 (1998).

Henseler, "The Genetics of Psoriasis", Journal of American Academy of Dermatology, vol. 37, No. 2, pp. S1-S11, 1997.

Henseler, and Christophers, "Disease Concomitance in Psoriasis", Journal of American Academy of Dermatology, vol. 32, pp. 982-986, 1997.

Henseler, and Christophers, "Psoriasis of Early and Late Onset: Characterization of Two Types of Psoriasis Vulgaris", Journal of American Academy of Dermatology, vol. 13, No. 3, pp. 450-456, 1995.

Herbin, et al., "Automated Registration of Dissimilar Images: Application to Medical Imagery", Computer Vision, Graphics, and Image Processing, vol. 47, pp. 77-88, 1989.

Hewick, et al., "A Gas-Liquid Solid Phase Peptide and Protein Sequentor", J. Biol. Chem., 256(15), 7990-7997 (1981).

Hiramine, et al., "Differential Effect of Cyclosporine in Vivo on the Distribution of T cell Subsets in the Thymus, Spleen, and Lymph Nodes", Transplatation, vol. 47, No. 3, pp. 499-503, 1989.

Hirano, et al., "Individual Pharmacodynamics Assessed by Antilymphocyte Action Predicts Clinical Cyclosporine Efficacy in Psoriasis", Clinical Pharmacology & Therateutics, vol. 63, No. 4, pp. 465-470, 1998.

Ho, et al., "Intermittent Short Courses of Cyclosporin (Neoral.RTM.) for Psoriasis Unresponsive to Topical Therapy: A 1-Year Multicentre, Randomized Study", British Journal Of Dermatology, vol. 141, pp. 283-291, 1999.

Hoffmann, et al., "Initiation and perpetuation of rat adjuvant arthritis is inhibited by the anti-CD2 monoclonal antibody (mAb) OX34", Annals of Rheumatic Diseases, 56 (12) : 716-722 (1997).

Hollsberg, et al., "Increased protein kinase C activity in human memory T cells", Cell. Immunol. 149(1):170-179 (1993).

Honeyman, et al., "Low-Dose Cyclosporine a Improves Severe Disabling Psoriasis in Latin America", International Journal of Dermatology, vol. 34, pp. 583-588, 1995.

Hooks et al., "Muromonab CD-3: A review of its pharmacology, pharmacokinetics, and clinical use in transplantation", Pharmacotherapy 11(1):25-37 (1991).

Hopkins, et al., "A double-Blind Controlled Trial of Etretinate (Tigason) and Ibuprofen in Psoriatic Arthritis", Annals of the Rheumatic Diseases, vol. 44, pp. 189-193, 1985.

Howard et al. (1981) A human T lymphocyte differentiation marker defined by monoclonal antibodies that block E-rosette formation: J. Immunol. 126(6):2117-2122.

Hughes et al. (1990) "Endothelial Cells Augment T Cell Interleukin 2 production by a Contact-Dependent Mechanism involving CD2/LFA-3 Interaction" J. Exp. Med. 171:1453-1467.

Hughes et al. (1990) "The Endothelial Cell As A Regulator Of T-Cell Function" Immunol. Rev. 117, 85-102.

Hugot, et al., "Mapping of a Susceptibility Locus for Crohn's Disease on Chromosome 16", Nature, vol. 379, pp. 821-823, 1996.

Hunt, et al., "Generalized Pustular Psoriasis Responsive to PUVA and Oral Cyclosporin Therapy", Australasian Journal of Dermatology, vol. 38, pp. 199-201, 1997.

Hyman (1985) "Cell-surface-antigen mutants of haematopoietic cells",Biochem J., vol. 225, pp. 27-40.

Ieiri et al., "Evaluation of the Therapeutic Range of Whole Blood Cyclosporin Concentration in the Treatment of Psoriasis", International Journal of Clinical Pharmacology and Therateutics, vol. 34, No. 3, pp. 106-111, 1996.

Ikemizu, et al., "Crystal Structure of the CD2-Binding Domain of CD58 (Lymphocyte Function-Associated Antigen 3) at 1.8-.ANG. Resolution", Proceedings of the National Academy of Science, vol. 96, pp. 4289-4294, 1999.

Inoue, et al., "Anti-adhesion molecule therapy in Theiler's murine encephalomyelitis virus-induced demyelinating disease", Int. Immunol. 9(12):1837-1847 (1997).

International Searching Authority, International Search Report for International Application No. PCT/US88/01924, dated Oct. 7, 1988.

International Searching Authority, International Search Report for International Application No. PCT/US89/03652, dated Feb. 7, 1990.

International Searching Authority, International Search Report for International Application No. PCT/US92/02050, dated Aug. 12, 1992.

International Searching Authority, International Search Report for International Application No. PCT/US92/08754, dated Jun. 28, 1993.

International Searching Authority, International Search Report for International Application No. PCT/US92/08755, dated Jul. 8, 1993.

International Searching Authority, International Search Report for International Application No. PCT/US99/20026, dated May 8, 2000.

International Searching Authority, International Search Report for International Application No. PCT/US02/02314, dated Jun. 11, 2002.

International Searching Authority, International Search Report for International Application No. PCT/US02/21631, dated Jun. 25, 2003.

International Searching Authority, International Search Report for International Application No. PCT/US05/16265, dated Oct. 26, 2005.

International Searching Authority, International Search Report for International Application No. PCT/US05/15531, dated Feb. 24, 2006.

International Searching Authority, International Search Report for International Application No. PCT/US05/03907, dated Oct. 3, 2005.

International Searching Authority, International Search Report for International Application No. PCT/US05/39070, dated Apr. 27, 2007.

Ip, et al., Structural Characterization of the N-Glycans of a Humanized Anti-CD18 Murine Immunoglobulin G, Archives of Biochemistry and Biophysics, vol. 308, No. 2, pp. 387-399, 1994.

Isaacs, et al., "Humanized Anti-CD4 Monoclonal Antibody Therapy of Autoimmune and Inflammatory Disease", Clinical and Experimental Immunology, vol. 110, pp. 158-166, 1997.

Jefferis, and Lund, "Glycosylation of Antibody Molecules: Structural and Functional Significance", Chemical Immunology, vol. 65, pp. 111-113, 1997.

Jemec, and Wulf, "The Applicability of Clinical Scoring Systems: SCORAD and PASI in Psoriasis and Atopic Dermatitis", Acta Derm Venereol (Stockholm), vol. 77, pp. 392-393, 1997.

Jenkins, et al., "CD28 Delivers A Constimulatory Signal Involved in Antigen-Specific IL-2 Production by Human T Cells", The Journal of Immunology, vol. 147(8), pp. 2461-2466, 1991.

Johnson, "On Teaching Dermatology to Nondermatologists", Arch Dermatol, vol. 130, pp. 850-852, 1994.

Jones, et al., "Crystal Structure at 2.8.ANG. Resolution of a Soluble Form of the Cell Adhesion Molecule CD2" Nature, vol. 360, pp. 232-239, 1992.

Jonker, "Immunosuppressive Therapy by monoclonal anti-T lymphocyte subset antibodies", Leukocyte Typing III (Oxford Univ. Press 1987) pp. 923-927.

Jonker, et al., "The Influence of OKT8F Treatment on Allograft Survival in Rhesus Monkeys", Transplantation 41(4): 431-435 (1986).

Jonker, et al., "Effects of in vivo administration of monoclonal antibodies specific for human T cell subpopulations on the immune system in a rhesus monkey model", Transplantation 35(6): 521-526 (1983).

June, "Increases in Tyrosine Phosphorylation are Detectable Before Phospholipase C Activation After T Cell Receptor Stimulation", The Journal of Immunology, vol. 144, No. 5, pp. 1591-1599, 1990.

Kang, et al., "Calcipotriene-Induced Improvement in Psoriasis is Associated with Reduced Interleukin-8 and Increased Interleukin-10 levels within Lesions", British Journal of Dermatology, vol. 138, pp. 77-83, 1998.

Kanner, et al., "CD2/LFA-3 Ligation Induces Phospholipase-C. gamma.1 Tyrosine Phosphorylation and Regulates CD3 Signaling", The Journal of Immunology, vol. 148, No. 7, pp. 2023-2029, 1992.

Kantor, et al., "Double-Blind Bilateral Paired Comparison of 0.05% Halobetasol Propionate Cream and its Vehicle in Patients with Chronic Atopic Dermatitis and Other Eczematous Dermatoses", Journal of the American Academy of Dermatology, vol. 25, No. 6, pp. 1184-1186. 1991.

Kaplan et al. (1987) "Distribution and Turnover of Langerhans Cells During Delayed Immune Responses in Human Skin" J. Exp. Med. 165:763-776.

Kaplon et al. (1996) "Short course single agent therapy with an LFA-3-IgG.sub.I fusion protein prolongs primate cardiac allograft survival." Tranplantation 61(3): 356-363.

Kasahara, et al., "Role of interleukin 6 for differential responsiveness of naive and memory CD4+ T cells in CD2-mediated activation", J. Exp. Med. 172 (5):1419-1424 (1990).

Kato, et al., "CD48 is a Counter-Receptor for Mouse CD2 and is Involved in T Cell Activation", Journal of Experimental Medicine, vol. 176, pp. 1241-1249, 1992.

Kaufman, and Sharp, "Amplification and Expression of Sequences of Cotransfected with a Modular Dihydrofolate Reductase Complementary DNA Gene", Journal of Molecular Biology, vol. 159, pp. 601-621, 1982.

Kaufman, and Sharp, "Construction of a Modular Dihydrofolate Reductase cDNA Gene: Analysis of Signals Utilized for Efficient Expression", Molecular and Cellular Biology, vol. 2, No. 11, pp. 1304-1319, 1982.

Kawai, et al., "Intrathecal administration of antibodies against LFA-1 and against ICAM-1 suppresses experimental allergic encephalomyelitis in rats", Cell Immunol. 171(2):262-268 (1996).

Kelso, Th1 and Th2 Subsets: Paradigms Lost?, Immunology Today, vol. 16, No. 8, pp. 374-379, 1995.

Kent, S. B. H., "Chemical Synthesis of Peptides and Proteins," Ann. Rev. Biochem., 57, pp. 957-989 (1988).

Kileen et al., "The MRC OX-45 Antigen of Rat Leukocytes and Endothelium is in a Subset of the Immunoglobulin Superfamily with CD2, LFA-3 and Carcinoembryonic Antigens", The EMBO Journal, vol. 7, No. 10, pp. 3087-3091, 1988.

Kimball ,Introduction to Immunology, 1983, (Ed.), Macmillan Publishing Co., New York, NY, 1983.

Kingston, et al., "Etretin Therapy for Severe Psoriasis", Arch Dermatol, vol. 123, pp. 55-58, 1987.

Kirkham, et al., "Chimeric CD7 monoclonal antibody therapy in Rheumatoid arthritis", J. Rheumatol. 19(9) 1348-1352 (1992).

Knox, et al., "Observations on the effect of chimeric anti-CD4 monoclonal antibody in patients with mycosis fungoides", Blood 77(1):20-30 (1991).

Kohler, G. and C. Milstein, "Continuous Cultures of Fused Cells Secreting Antibody of Predefined Specificity," Nature, 256, pp. 495-497 (Aug. 7, 1975).

Kollias, "Letter to the Editor: Simple Changes to PUVA Phototherapy May Minimize to the Photocarcinogenic Risks", Photodermatology, Photoimmunology, & Photomedicine, vol. 15, pp. 205, 1999.

Koo, "Neoral in Psoriasis Therapy: Toward a New Perspective", International Journal of Dermatology, vol. 36, pp. 25-29, 1997.

Koo, "Population-Based Epidemiological Study of Psoriasis with Emphasis on Quality of Life Assessment", Psychodermatology, vol. 14, No. 3, pp. 485-496, 1996.

Koo, "Systematic Sequential Therapy of Psoriasis: A New Paradigm for Improved Therapeutic Results", Journal of the American Academy of Dermatology, vol. 41, No. 3, pp. S25-S28, 1999.

Koo, et al., "Mometasone Furoate 0.1%-Salicylic Acid 5% Ointment Versus Mometasone Furoate 0.1% Ointment in the Treatment of Moderate-to-Severe Psoriasis: A Multicenter Study", Clinical Therapeutics, vol. 20, No. 2, pp. 283-291, 1998.

Koshy, et al., "Increased Expression of CD40 Ligand on Systemic Lupus Erythematosus Lymphocytes", Journal of Clinical Investigation, vol. 98, No. 3, pp. 826-837, 1996.

Koyasu et al. (1990), "Role of Interaction Of CD2 Molecules With Lymphocyte Function-Associated Antigen 3 in T-Cell Recognition of Nominal Antigen" Proc. Natl. Acad. Sci. USA 87: 2603-2607.

Kraan et al., "Alefacept Treatment in Psoriatic Arthritis" Arthritis Rheum. 46(10):2776-2784 (2002).

Kragballe, et al., "A Double-Blind Comparison of Acitretin and Etretinate in the Treatment of Severe Psoriasis", Acta Derm Venereol (Stockh), vol. 69, pp. 35-40, 1989.

Kranz et al., "Immunoprecipitation of Cell Surface Structures of Cloned Cytotoxic T Lymphocytes by Clone-Specific Antisera," Proc. Natl. Acad. Sci. U.S.A., vol. 81, pp. 573-577 (1984).

Krensky (1990) "The Human Cytolytic T Lymphocyte Response to Transplantation Antigens" Pediatric Res. 19(12):1231-1234.

Krensky et al. (1983) "The Functional Significance, Distribution, And Structure Of LFA-1, LFA-2, and LFA-3: Cell Surface Antigens Associated With CTL-Target Interactions" J. Immunol. 131(2):611-616.

Krensky et al. (1984) "Human Lymphocyte Function Associated Antigens" Surv. Immunol. Res. 3:39-44.

Krueger, et al., "Anti-CD11a treatment for psoriasis concurrently increases circulating T-cells and decreases plaque T-cells, consistent with inhibition of cutaneous T-cell trafficking", J. Inves. Derm. 115:333 (2000) (Abstract).

Krueger "Efficacy and Safety results of a phase II trial with LFA3TIP in patients with chronic plaque psoriasis." Am Acad Dermatol. 58th Ann Meeting Mar. 10-15, 2000. (Abstract).

Krueger, and Duvic, "Epidemiology of Psoriasis: Clinical Issues", The Journal of Investigative Dermatology, vol. 102, No. 6, pp. 14S-18S, 1994.

Krueger, Efficacy and Safety results of a phase II trial with LFA3TIP in patients with chronic plaque psoriasis. From Gene to Clinic Congress. AMEVIVE™ Breakfast Meeting Dec. 3, 1999 p. 1.

Krueger, et al., "The Safety and Efficacy of Tazarotene Gel, a Topical Acetylenic Retinoid, in the Treatment of Psoriasis", Arch Dermatol, vol. 134, pp. 57-60, 1998.

Kullavanijaya, and Kulthanan, "Clinical Efficacy and Side Effects of Acitrctin on the Disorders of Keratinization: A One-Year Study", The Journal of Dermatology, vol. 20, pp. 501-506, 1993.

Kumar, et al., "Methotrexate in Childhood Psoriasis", Pediatric Dermatology, vol. 11, No. 3, 271-273, 1994.

Kumar, et al., "Short Term Methotrexate Therapy in Psoriasis", Indian J Med Res, vol. 100, pp. 277-280, 1994.

Kupper, "Immune and inflammatory processes in cutaneous tissues: mechanisms and speculations", J.Clin. Invest. 86:1783-1789 (1990).

Laburte, et al., "Efficacy and Safety of Oral Cyclosporin A (CyA; Sandimmun.RTM.) for Long-Term Treatment of Chronic Severe Plaque Psoriasis", British Journal of Dermatology, vol. 130, pp. 366-375, 1994.

Lai et al., "Two Forms of TB236/Myelin-Associated Glyco Protein, a Cell Adhesion Molecule for Postnatal Neural Development, are Produced by Alternative Splicing," Proc. Natl. Acad. Sci. U.S.A., 84, pp. 4337-4441 (1987).

Lai et al., "Solid-State Chemical Stability of Proteins and Peptides", Journal of Pharmaceutical Sciences, vol. 88, No. 5, pp. 489-500, 1999.

Lambert, et al., "Safety and Pharmacokinetics of Hyperimmune Anti-Human Immunodeficiency Virus (HIV) Immunoglobulin Administered to HIV-Infected Pregnant Women and Their Newborns", The Journal of Infectious Diseases, vol. 175, pp. 283-291, 1997.

Lambert, J. M. et al., "Purified Immunotoxins That Are Reactive With Human Lymphoid Cells," J. Biol. Chem., 260(22), pp. 12035-12041 (1985).

Langford, et al., "Use of Cytotoxic Agents and Cyclosporine in the Treatment of Autoimmune Disease", Annals of Internal Medicine, vol. 129, No. 1, pp. 49-58, 1998.

Lanigan, "Treatment of Psoriasis with the Pulsed Dye Laser", Journal of the American Academy of Dermatology, vol. 37, No. 2, pp. 288-289, 1997.

Larson and Springer (1990) "Structure and function of leukocyte integrins" Immunol. Revs. 114:181-217.

Lauharanta, and Geiger, "A Double-Blind Comparison of Acitretin and Eretinate in Combination with Bath PUVA in the Treatment of Extensive Psoriasis", British Journal of Dermatology, vol. 121, 107-112, 1989.

Lauharanta, et al., "A Clinical Evaluation of the Effects of an Aromatic Retinoid (Tigason), Combination of Retinoid and PUVA, and PUVA Alone in Severe Psoriasis", British Journal of Dermatology, vol. 104, pp. 325-332, 1981.

Le et al. (1987) "Anti-LFA-3 Monoclonal Antibody Induced Interleukin 1 (IL 3) Release by Thymic Epithelial (TE) Cells and Monocytes" FASEB J. 46(3):447 Abstract 761.

Le et al. (1990) "Ligan Binding to the LFA-3 Cell Adhesion Molecule Induces II-1 Production by Human Thymic Epithelial Cells" J. Immunol. 144:4541-4547.

Lebwohl, et al., "Interactions Between Calcipotriene and Ultraviolet Light", Journal of the American Academy of Dermatology, vol. 37, No. 1, pp. 93-95, 1997.

Lebwohl, et al., "Once-Daily Tazarotene Gel Versus Twice-Daily Flucinonide Cream in the Treatment of Plaque Psoriasis", Journal of the American Academy of Dermatology, vol. 38, No. 5, pp. 705-711, 1998.

Ledo, et al., "Acitretin (Ro 10-1670) in the Treatment of Severe Psoriasis: A Randomized Double-Blind Parallel Study Comparing Acitrecin and Eretinate", International Journal of Psoriasis, vol. 27, No. 9, pp. 656-659, 1988.

Lemster, et al., "FK 506 Inhibits Cytokine Gene and Adhesion Molecule Expression in Psoriatic Skin Lesions", Annals of New York Academy of Sciences, vol. 696, pp. 250-256, 1993.

Lennard-Jones, "Defining Ulcer Depth in Colitis", The Lancet, vol. 347, pp. 1708, 1996.

Letvin, et al., "T Lymphocyte Surface Antigens in Primates", European Journal of Immunology, vol. 13, pp. 345-347, 1983.

Ley, et al., "The T Cell Receptor/CD3 Complex and CD2 Stimulate the Tyrosine Phosphorylation of Indistinguishable Patterns of Polypeptides in the Human T Leukemic Cell Line Jurkat", European Journal of Immunology, vol. 21, pp. 2203-2209, 1991.

Li, et al., "Enhancement of B cell responses by the interaction of CD2 with LFA-3", J. Tongji Med. Univ. 12(2):71-74 (1992).

Liao, T., et al., "Modification of Sialyl Residues of Sialoglycoprotein(s) of the Human Erythrocyte Surface," J. Biol. Chem., 248(23), pp. 8247-8253 (Dec. 10, 1973).

Lichtiger, et al., "Cyclosporine in Severe Ulcerative Colitis Refractory to Steroid Therapy", The New England Journal of Medicine, vol. 330, No. 26, pp. 1841-1845, 1994.

Lindelof, "Risk of Melanoma with Psoralen/Ultraviolet A Therapy for Psoriasis", Drug Safety, vol. 20, No. 4, pp. 289-297, 1999.

Llewellyn-Smith, et al., "Effects of Anti-CD4 Antibody Treatment on Lymphocyte Subsets and Stimulated Tumor Necrosis Factor Alpha Production: A Study of 29 Multiple Sclerosis Patients Entered into a Clinical Trial of cM-T412", Neurology, vol. 48, pp. 810-816, 1997.

Lorincz, "Cutaneous T-Cell Lymphoma (Mycosis Fungoides)", the Lancet, vol. 347, pp. 871-876, 1996. •.

Lotti, et al., "Neuropeptides and Skin Disorders. The New Frontiers of Neuro-Endocrine-Cutaneous Immunology", International Journal of Dermatology, vol. 38(9), pp. 673-675, 1999.

Low, "Biochemistry of the Glycosyl-Phosphatidylinositol Membrane Protein Anchors," Biochem. J., 244, pp. 1-13 (1987).

Lowe, "Initiating Neoral.RTM. Therapy", International Journal of Dermatology, vol. 36(suppl. 1), pp. 30-33, 1997.

Ludden, "Population Pharmacokinetics", Journal of Clinical Pharmacology, vol. 28, pp. 1059-1063, 1998.

Mackay, et al., "Naive and Memory T Cells Show Distinct Pathways of Lymphocyte Recirculation", J Exp Med. Mar. 1, 1990;171(3):801-17.

Magilavy, et al., "Targeting CD2 for immunotherapy: results of a phase 1 trial with a LFA-3/IgG Fe fusion protein", Arthritis Rheum. 40(9-suppl.): S176 (1997) (Abstract).

Magilavy, et al., "Pharmacodynamic effects of LFA3TIP (Amevive) in patients with chronic plaque psoriasis (CPP) : Selective modulation of CD45RO+lymphocytes", J. Invest. Dermatol 112(4):609 (1999) (Abstract).

Mahrle, et al., "Anti-Inflammatory Efficacy of Low-Dose Cyclosporin A in Psoriatic Arthritis. A Prospective Multicentre Study", British Journal of Dermatology, vol. 135, pp. 752-757, 1996.

Majeau et al. (1994), "Mechanism of lymphocyte function-associated molecule 3-Ig fusion proteins inhibition of T cell responses," J. of Immunol. 152 (6): 2753-2767 (1994).

Majeau, et al., "Low Affinity Binding of an LFA-3/IgG1 Fusion Protein to CD2+ T Cells is Independent of Cell Activation", Cell Adhesion and Communication, vol. 7, No. 3, pp. 267-279, 1999.

Majewski, et al., "Papillomavirus and Autoimmunity in Psoriasis", Immunology Today, vol. 20, No. 10, pp. 475-476, 1999.

Makgoba et al. (1989) "The CDA2-LFA-3 And LFA-1-ICAM Pathways: Relevance to T-Cell Recognition" Immunol. Today 10(12):417-422.

Makgoba et al., "Human T Cell Rosetting is Mediated by LFA-3 on Autologous Erythrocytes," Journ. Immunol., vol. 138(11), pp. 3587-3589 (1987).

Maniatis, et al., "Extraction, Purification, and Analysis of mRNA from Eukaryotic Cells", Molecular Cloning, A Laboratory Manual 187-209 (Cold Spring Harbor Laboratory, 1982).

March, et al., "A Simplified Method for Cyanogen Bromide Activation of Agarose for Affinity Chromatography", Anal. Biochem., 60, 149-152 (1974).

Martz and Gromkowski (1985) "Lymphocyte Function-Associated Antigens: Regulation of Lymphocyte Adhesions In Vitro And immunity In Vivo" Mechanisms of Cell-Mediated Cytotoxicity II (Plenium Press, 1985) pp. 291-310.

Matis (1990) "The molecular basis of T-cell specificity" Ann. Rev. Immunol. 8:65-82.

Matsuyama, et al., "The Quantitative and Qualitative Defect of CD4+ CD45RO+ Memory-Type T Cells are Involved in the Abnormality of TH1 Immunity in Atopic Dermatitis Patients", Clinical and Experimental Allergy, vol. 29, pp. 687-694, 1999.

Maxam et al., "Sequencing End-Labeled DNA with Base-Specific Chemical Cleavages", Methods in Enzymology, 65:499-560 (Academic Press,1980).

Maxam, et al., "A New Method for Sequencing DNA", Proc. Natl. Acad. Sci., 74, 560-564 (1977).

Mazzanti, et al., "Methotrexate and Cyclosporin Combined Therapy in Severe Psoriatic Arthritis. A Pilot Study", Acta Derm Venereol (Stockh), Suppl. 186, pp. 116-117, 1994.

McFarland, "Complexities in the Treatment of Autoimmune Disease", Science, vol. 274, pp. 2037-2038, 1996.

Meffert, and Sonnichsen, "Acitrecin in the Treatment of Severe Psoriasis: A Randomized Double-Blind Study Comparing Acitrecin and Etretinate", Acta Derm Venereol (Stockh), Suppl.146, pp. 176-177, 1989.

Meffert, et al., "Low-Dose (1.25 mg/kg) Cyclosporin A: Treatment of Psoriasis and Investigation of the Influence on Lipid Profile", Acta Derm Venereol (Stockh), vol. 77, pp. 137-141, 1997.

Meier et al (1995) "Immunomodulation by LFA3TIP, an LFA-3/IgG.sub.1 fusion protein: cell line dependent glycosylation effects on pharmacokinetics and pharmacodynamic markers," Therapeutic Immunology 2(2): 159-171.

Meingassner, et al., "A Novel Anti-Inflamatory Drug, SDZ ASM 981, for the Topical and Oral Treatment of Skin Diseases: In Vivo Pharmacology", British Journal of Dermatology, vol. 137, pp. 568-576, 1997.

Menter, and Barker, "Psoriasis Practice", The Lancet, vol. 338, pp. 231-234, 1991.

Merck Manual, Seventeenth Ed. pp. 303-313, 448, 725-729, 1474-1476.

Mesalamine Study Group, "An Oral Preparation of Mesalamine as Long-Term Maintenance Therapy for Ulcerative Colitis: A Randomized Placebo-Controlled Trial", Annals of Internal Medicine, vol. 124, pp. 204-211, 1996.

Meuer et al. (1984) "An Alternative Pathway of T Cell Activation: A Functional Role for the 50 kd TII Sheep Erythrocyte Receptor Protein" Cell 36:897-906.

Meuer et al. (1984) "The human T-cell receptor" Ann. Rev. Immunol. 2:23-50.

Meuer et al. (1989) "The Alternative Pathway of T Cell Activation: Biology, Pathophysiology, and Perspectives for Immunopharmacology" Clin. Immunol. Immunopath. 50:S133-S138.

Michler, et al. "Pretransplant blood transfusion in a primate cardiac xenograft model", Curr. Surg. 44(1):42-45 (1987).

Michler, et al., "Technique for primate heterotopic cardiac xenotransplantation", J. Med. Primatol. 14:357-362 (1985).

Michler, et al., "Prolongation of primate cardiac xenograft survival with cyclosporine", Transplantation 44(5):632-636 (1987).

Mikayama, et al., "Molecular cloning and functional expression of a cDNA encoding glycosylation-inhibiting factor", PNAS 90:10056-10060 (1993).

Miller et al. (1993) "Specific interaction of lymphocyte function associated antigen 3 with CD2 can inhibit T cell responses," J. Exp. Med. 178: 211-222.

Moingeon et al. (1989) "The Structural Biology of CD2" Immunol. Rev. 111:111-144.

Moingeon et al. (1989), "CD2-mediated adhesion facilitates T lymphocyte antigen recognition function," Nature 339: 312-339.

Moingeon et al. (1991) "Complementary Roles for CD2 And LFA-1 Adhesion Pathways During T Cell Activation" Eur. J. Immunol. 21:605-610.

Mordenti, "Forecasting Cephalosporin and Monobactam Antibiotic Half-Lives in Humans from Data Collected in Laboratory Animals", Antimicrobial Agents and Chemotherapy, vol. 27, No. 6, pp. 887-891, 1985.

Moreland, et al. "Use of a chimeric monoclonal anti-CD4 antibody in patients with refractory rheumatoid arthritis", Arthritis and Rheumatism 36(3) (1993).

Moreland, et al., "Biological Agents for Treating Rheumatoid Arthritis", Arthritis and Rheumatism, vol. 40, No. 3, pp. 397-409, 1997.

Morison, et al., "Consensus Workshop on the Toxic Effects of Long-Term PUVA Therapy" Arch Dermatol, vol. 134, pp. 595-598, 1998.

Moroney, S. E., et al., "Modification of the Binding Site(s) of Lectins by an Affinity Column Carrying an Activated Galactose-Terminated Ligand," Biochemistry, 26, pp. 8390-8398 (1987).

Morrison, S. L., "Transfectomas Provide Novel Chimeric Antibodies," Science, 229, pp. 1202-1207 (Sep. 20, 1985).

Mosmann, et al., "The Expanding Universe of T-Cell Subsets: Th1, Th2 and More", Immunology Today, vol. 17, No. 3, pp. 138-145, 1996.

Mrowietz, et al., "Long-Term Maintenance Therapy with Cyclosporine and Posttreatment Survey in Severe Psoriasis: Results of a Multicenter Study", Journal of the American Academy of Dermatology, vol. 33, No. 3, pp. 470475, 1995.

Muchenberger, et al., "The Combination of Oral Acitrecin and Bath PUVA for the Treatment of Severe Psoriasis", British Journal of Dermatology, vol. 137, pp. 587-589, 1997.

Mulligan et al., "Selection for Animal Cells that Express the *Escherichia coli* Gene Coding for Xanthine-Guanine Phophoribosyltransferase", Proc. Natl. Acad. Sci. U.S.A., 78:2072-2076 (1981).

Murray, et al., "A 12-Month Treatment of Severe Psoriasis with Acitrecin: Results of a Canadian Open Multicenter Study", Journal of the American Academy of Dermatology, vol. 24, No. 4, pp. 598-602, 1991.

Mussi, et al., "Serum TNF-Alpha Levels Correlate with Disease Severity and are Reduced by Effective Therapy in Plaque-Type Psoriasis", J Biol Regul Homeost Agents, vol. 11, No. 3, pp. 115-118, 1997.

Nair, et al., "Evidence for Two Psoriasis Susceptibility Loci (HLA and 17q) and Two Novel Candidate Regions (16q and 20p) by Genome-Wide Scan", Human Molecular Genetics, vol. 6, No. 8, pp. 1349-1356, 1997.

Nakakura, et al., "Potent and effective prolongation by anti-LFA-1 monoclonal antibody monotherapy of non-primarily vascularized heart allograft survival in mice without T cell depletion", Transplantation 55(2):412-417 (1993).

Naldi, et al., "Analytical Epidemiology in Psoriasis", Journal of Investigative Dermatology, vol. 102, No. 6, pp. 19S-23S, 1994.

Nathan et al. (1986) "Local and Systemic Effects of Intradermal Recombinant Interferon-.gamma. in Patients with Lepromatous Leprosy" New Eng. J. Med. 315(1):6-15.

Neuberger et al., "Recombinant antibodies possessing novel effector functions", 1984, Nature, vol. 312;604-608.

Ngo et al. "Computational complexity, protein structure prediction, and the Levinthal paradox" in The Protein Folding Problem and Tertiary Structure Prediction, 1994, Merz et al. (Ed.), Birkhauser, Boston, MA, pp. 433 and 492-495, 1994.

Nicholas, et al., "CD4 antibody treatment of severe psoriasis", Lancet 338:321 (1991).

Nickoloff, "The Cytokine Network in Psoriasis", Arch Dermatol, vol. 127, pp. 871-884, 1991.

Nickoloff, et al., "Accessory Cell Function of Keratinocytes for Superantigens: Dependence on Lymphocyte Function-Associated Antigen-1/Intercellular Adhesion Molecule-1 Interaction", The Journal of Immunology, vol. 150, No. 6, pp. 2148-2159, 1993.

Nickoloff, et al., "Cytokine Networks: Immunobiology Surfaces", The Journal of NIH Research, vol. 3, pp. 71-74, 1991.

Nishibu, et al., "Overexpression of Monocyte-Derived Cytokines in Active Psoriasis: A Relation to Coexistent Arthropathy", Journal of Dermatological Science, vol. 21, pp. 63-70, 1999.

Nouri et al. (1990) "Selective and non-selective loss of immunoregulatory molecules (HLA-A,B,C antigens and LFA-3) in transitional cell carcinoma" J. Br. Cancer 62:603-606.

O'Gorman, et al., "Genetic Polymorphisms associated with clinical improvement of chronic plaque psoriasis after treatment with alefacept", J. Inves. Derm. 124(4): A40 (2005) (Abstract).

Okayama, et al., "High-Efficiency Cloning of Full-Length cDNA", Mol. Cell. Biol., 2(2): 161-170 (1982).

Olivieri, et al., "Therapy with Cyclosporine in Psoriatic Arthritis", Seminars in Arthritis and Rheumatism, vol. 27, No. 1, pp. 36-43, 1997.

Osband et al. (1990) "Problem in the investigational Study and Clinical Use of Cancer Immunotherapy" Immunology today 11(6): 193-195.

Osborn et al. (1995), "Amino acid residues required for binding of lymphocyte function-associated antigen 3 (CD58) to its counter-receptor CD2," J. Exp. Med. 181(1): 429-434.

Park, and Youn, "Factors Influencing Psoriasis: An Analysis Based upon the Extent of Involvement and Clinical Type", The Journal of Dermatology, vol. 25, pp. 97-102, 1998.

Patel, et al., "Compatibility of Calcipotriene with Other Topical Medications", Journal of the American Academy of Dermatology, vol. 38, No. 6, pp. 1010-1011, 1998.

Pavli, et al., "Inflammatory Bowel Disease: Germs or Genes?", The Lancet, vol. 347, pp. 1198, 1996.

Pearson, et al., "Azathioprine and 6-Mercaptopurine in Crohn Disease: A Meta-Analysis", Annals of Internal Medicine, vol. 122, pp. 132-142, 1995.

Peckham, et al., "The Treatment of Severe Psoriasis", Arch Dermatol, vol. 123, pp. 1303-1307, 1987.

Peng, et al., "Ligation of CD2 provides a strong helper signal for the production of the type 2 cytokines", Cell. Immunol., 181(1):76-85 (1997).

Pepino et al. (1989) "Primate Cardiac Allo- and Xenotransplantation: Modulation of the Immune Response with Photochemotheraphy" Eur. Surg. Res. 21:105-113.

Pepinsky et al. (1991), "The increased potency of cross-linked lymphocyte function-associated antigen-3 (LFA-3) multimers is a direct consequence of changes in valency," J. Biol Chem. 266(27): 18244-18249.

Pepinsky, et al., "Purification and Partial Sequence Analysis of a 37-kDA Protein that Inhibits Phospholipase A.sub.2 Activity from Rat Peritoneal Exudates", J. Bio. Chem., 261(9), 4239-4246 (1986).

Peterson (1987) "Monoclonal Antibody and Ligand Binding Sites Of The T Cell Erythrocyte Receptor (CD2)" Nature 329:842-846.

Peterson, A. S., "Genetic and Biochemical Analysis of CD2, LFA-3 Interation," In Genetic Analysis of CD2/LFA and CD4/HIV Interactions, Chapter 1, pp. 1-13, Figure 1A (Harvard University, Cambridge, Massachusetts 1988).

Pettit, "Oral Retinoid for Psoriasis: A Report of a Double Blind Study", Acta Derm Venereol Suppl (Stockh). 1979;59(85):133-6.

Petzelbauer, et al., "Cyclosporin A Suppresses ICAM-1 Expression by Papillary Endothelium in Healing Psoriatic Plaques", The Journal of Investigative Dermatology, vol. 96, No. 3, pp. 362-386, 1991.

Picker et al. (1990) "A Unique Phenotype of Skin-associated Lymphocytes in Humans" Am. J. Path. 136(5):1053-1068.

Pitzalis, "Skin and joint disease in psoriatic arthritis: What is the link?" Br. J. Rheum. 37(5): 480-483 (1998).

Pitzalis, et al., "Selective Migration of the Human Helper-Inducer Memory T Cell Subset: Confirmation by In Vivo Cellular Studies", European Journal of Immunology, vol. 21, pp. 369-376, 1991.

Platt, et al. "Transplantation of discordant xenografts: a review of progress", lmmunol. Today 11(12):450-456 (1990).

Podolsky, "Inflammatory Bowel Disease", The New England Journal of Medicine, vol. 325, No. 13, pp. 928-1014, 1991.

Poikolainen, et al., "Excess Mortality Related to Alcohol and Smoking Among Hospital-Treated Patients with Psoriasis", Arch Dermatol, vol. 135, pp. 1490-1493, 1999.

Poizot-Martin et al. (1991) "Are CD4 antibodies and peptide T new treatments for psoriasis" The Lancet 337:1477.

Polito, et al., "Preliminary Evidence for Genetic Anticipation in Crohn's Disease", The Lancet, vol. 347, pp. 798-800, 1996.

Prens, et al., "T Lymphocytes in Psoriasis", Clinics in Dermatology, vol. 13, pp. 115-129, 1995.

Prentice "Deaths Linked to Growth Hormone" The Times (London), Apr. 6, 1991 (Cited for argument).

Prince (1989) "Requirement For Both The CD3/T Cell Receptor Complex And The CD2/Lymphocyte Function-Associated Antigen-3 Adhesion System in Monocyte-Independent T Cell Activation by Oxidized Erythrocytes" Immunol. Investigations 18:1081-1093.

Prinz et al. (1991) "Chimaeric CD4 monoclonal antibody in treatment of generalised pustular psoriasis" The Lancet 338:320-321.

Prinz, "Which T Cells Cause Psoriasis?", Clinical and Experimental Dermatology, vol. 24, pp. 291-295, 1999.

Qin et al, "Induction of classical transplantation tolerance in the adult", J. Exp. Med. 169(3):779-794 (1989).

Queen et al, "A humanized antibody that binds to the interleukin 2 receptor", PNAS 86:10029-10033 (1989).

Ramakrishnan, S. and L. L. Houston, "Comparison of the Selective Cytotoxic Effects of Immunotoxins Containing Ricin A Chain or Pokeweed Antiviral Protein and Anti-Thy 1.1 Monoclonal Antibodies," Cancer Research, 44, pp. 201-208 (Jan. 1984).

Rao, et al., "C-Terminal Modification Occurs in Tissue Culture Produced OKT3", Biopharm-The Technology & Business of Biopharmaceuticals, 1991, V4, N10, p. 38-43.

Rau, et al., "Longterm combination therapy of refractory and destructive rheumatoid arthritis with methotrexate (MTX) and intramuscular gold or other disease modifying antirheumatic drugs compared to MTX monotherapy", J. Rheumatol. 25(8):1485-1492 (1998).

Recny et al. (1990) "Structural And Functional Characterization Of The CD2 lmmunoadhesion Domain" J. Biol. Chem. 265(15):8542-8549.

Reetsma, "Xenografts", Transplantation Proceedings 21(1):517-518 (1989).

Refsum, et al., "Fasting Plasma Homocysteine as a Sensitive Parameter of Antifolate Effect: A Study of Psoriasis Patients Receiving Low-Dose Methotrexate Treatment", Clinical Pharmacology Therapy, vol. 46, No. 5, pp. 510-520, 1989.

Reichlin, M., "Use of Glutaraldehyde as a Coupling Agent for Proteins and Peptides," In Methods in Enzymology, 70, edited by Van Vunakis et al., (Academic Press, New York, 1980) pp. 159-165 (1980).

Reichmann, et al., "Reshaping human antibodies for therapy", Nature 332:323-327 (1998).

Reilly, et al., "Compartmental Analysis of the Pharmacokinetics of Radioiodinated Monoclonal Antibody B72.3 in Colon Cancer Patients", Nucl. Med. Biol, vol. 20, No. 1, pp. 57-64, 1993.

Reilly, et al., "Problems of Delivery of Monoclonal Antibodies; Pharmaceutical and Pharmacokinetic Solutions", Clinical Pharmacokinetics, vol. 28, No. 2, pp. 126-142, 1995.

Reimann et al.; "In Vivo Administration of Lymphocyte-Specific Monoclonal Antibodies in Nonhuman Primates" (Transplantation—Dec. 1989 pp. 906-912).

Richardson, N.E., et al., "Adhesion Domain of Human T11 (CD2) is Encoded by a Single Exon," Proc. Natl. Acad. Sci. (USA), 85, pp. 5176-5180 (1988).

Riggs et al. (1996), "The pharmacokinetic/pharmacodynamic (PK/PD) modeling of immunoglobin fusion protein, LFA3TIP, using a non-linear saturable cell activity model," Pharmaceutical Research 13 (9 Supp.): s398 (Abstract).

Rincon and Patarroyo (1989) "Effect Of Antibodies From The T Cell (CD2' Only) And The Nk/Non-Lineage (New Panel Only) Sections On Adhesion Of Jurkat (T) Cell to Human Erythrocytes" Tissue Antigens 33:285.

Rivers, et al., "UVA Sunbeds: Tanning, Photoprotection, Acute Adverse Effects and Immunological Changes", British Journal of Dermatology, vol. 120, pp. 767-777, 1989.

Rodriguez, et al., "Optic Neuritis Posed a 40-Year Risk of 60% for Multiple Sclerosis", ACP Journal Club, vol. 122-123: 21, 1995.

Roitt, Immunology, Gower Medical Pub. (1985)—Immunology textbook.

Rose, "Risks of Cardiac Transplantation", Ann.Thoracic Surg. 47:645 (1989).

Rose, et al. "Immunosuppression in Cardiac Transplantation", Biblthca Cardiol. 43:1-9 (1988).

Rose, et al. "Humoral immune responses after cardiac transplantation: Correlation with fatal rejection and graft atherosclerosis", Surgery 106(1):203-208 (1989).

Rose, et al., "Cardiac Xenotransplantation", Prog. Cardiovasc. Diseases 33(2):105-117 (1990).

Rose, et al., "Present Status of Human Cardiac Allografts and Prospects for Xenografts", Trans Am. Soc. Artif. Intern. Organs 34:19-23 (1988).

Rudinger, J. "Characteristics of the amino acids as components of a peptide hormone sequence" in Peptide Hormones, Parson, J. A. (Ed.), University Park Press, Baltimore, MD, pp. 1-7, 1976.

Sachs, et al., "Immunology of Xenograft Rejection", Hum. Immunol. 28:245-251 (1990).

Salmi, et al., "Dual Binding Capacity of Mucosal Immunoblasts to Mucosal and Synovial Endothelium in Humans: Dissection of the Molecular Mechanisms", Journal of Experimental Medicine, vol. 181, pp. 137-149, 1995.

Salmi, et al., "Homing of Mucosal Leukocytes to Joints: Distinct Endothelial Ligands in Synovium Mediate Leukocyte-Subtype Specific Adhesion", Journal of Clinical Investigation, vol. 99, No. 9, pp. 2165-2172, 1997.

Sanchez-Madrid, F. et al., "Three Distinct Antigens Associated with Human T-Lymphocyte-Mediated Cytolysis: LFA-1, LFA-2, and LFA-3," Proc. Natl. Acad. Sci, USA, 79, pp. 7489-7493 (Dec. 1982).

Sander, et al., "The Annual Cost of Psoriasis", Journal of the American Academy of Dermatology, vol. 28, No. 3, pp. 422-425, 1993.
Sanders et al. (1988) "T Cell Adhesion Receptors LFA-1 And CD2 And Their Ligands ICAM-1 And LFA-3" Analysis in Adhesion, Cell Mediated Lysis, And As Markers OfT Cell Subsets in The T-Cell Receptor, A.R. Liss, Inc., pp. 269-279.
Sanders, et al., "Human Memory T Lymphocytes Express Increased Levels of Three Cell Adhesion Molecules (LFA-3, CD2, and LFA-1) and Three Other Molecules (UCHL1, CDw29, and Pgp-1) and have enhanced IFN-.gamma. Production", The Journal of Immunology, vol. 140, No. 5, pp. 1401-1407, 1988.
Savage et al. (1991), "Endothelial cell lymphocyte function-associated antigen-3 and an unidentified ligand act in concert to provide costimulation to human peripheral blood CD4.sup.+ T cells," Cellular Immunology 137(1): 150-163.
Sayre et al. (1987), "Molecular cloning and expression of T11 cDNAs reveal a receptor-like structure on human T lymphocytes" Chemical Abstracts 107(15): Abstract 128218x.
Sayre, et al. "Molecular cloning and expression of T11 cDNAs reveal a receptor-like structure on human T lymphocytes", PNAS 84:2941-2945 (1987).
Schneider, et al., (Abstract) "A pilot study of the safety and efficacy of Alefacept in subject with active rheumatoid arthritis on methotrexate" European League Against Rheumatism (2003).
Schopf (1986) "Stimulation of T Cells by Autologous Molecular Leukocytes and Epidermal Cells in Psoriasis" Arch. Dermatol. Res. 279:89-94.
Schopf, "Interactions between epidermal cells and lymphocytes in psoriasis", Immunology Today 7:358 (1988).
Schraven, et al., "Alternations of CD2 Association with T Cell Receptor Signaling Molecules in 'CD2 Unresponsive' Human T Lymphocytes", European Journal of Immunology, vol. 23, pp. 119-123, 1993.
Schwartz, et al., "Identification of the TS2/18-Recognized Epitope on the CD2 Molecule as a Target for Suppression of T Cell Cytokine Synthesis", The Journal of Immunology, vol. 154, pp. 5813-5820, 1995.
Schweighoffer, et al. "Adhesions cascades: diversity through combinatorial strategies", Curr. Opin. Cell. Biol. 4(5):824-829 (1991).
Seed, et al. (1987) "Molecular Cloning of the CD2 Antigen, The T-Cell Erythrocyte Receptor, By A Rapid immunoselection procedure" Proc. Natl. Acad. Sci. USA 84:3365-3369.
Seed, B. "An LFA-3 cDNA Encodes a Phospholipid-Linked Membrane Protein Homologous to its Receptor CD2," Nature, 329, pp. 840-842 (1987).
Seed, et al., "Molecular Cloning of the CD2 Antigen, the T-Cell Erythrocyte Receptor, By a Rapid Immunoselection Procedure," Proc. Natl. Acad. Sci. USA, 84, pp. 3365-3369 (May 1987).
Selvaraj et al. "Deficiency of Lymphocyte Function Associated Antigen 3 (LFA3) in Paroxysmal Nocutrnal Hemoglobinuria," J. Exp. Med., 166, pp. 1011-1025 (1987).
Selvaraj et al. (1987) "The T Lymphocyte Glycoprotein CD2 (LFA-2/T11/E-Rosette Receptor) Binds The Cell Surface Ligand LFA-3" FASEB J. 46(3):447 Abstract 760.
Selvaraj, P. et al., "The T Lymphocyte Glycoprotein CD2 Binds the Cell Surface Ligand LFA-3," Nature, 326, pp. 400-403 (Mar. 1987).
Semnani et al. (1994), "Costimulation by purified intercellular adhesion molecule 1 and lymphocyte function-associated antigen 3 induces distinct proliferation, cytokine and cell surface antigen profiles in human "naive" and "memory" CD4.sup.+ T cells," J. Exp. Med. 180:2125-2135.
Seo, "Evaluation of Disease Activity in Patients with Moderately Active Ulcerative Colitis: Comparisions Between a New Activity Index and Truelove and Witts' Classification", The American Journal Of Gastroenterology, vol. 90, No. 10, pp. 1759-1763, 1995.
Sewell et al. (1986) "Molecular Cloning Of The Human T-Lymphocyte Suface CD2 (T11) Antigen" Proc. Natl. Acad. Sci. USA 83:8718-8722.
Shahidullah, et al., "Etretinate Therapy for Psoriasis and Other Keratinizing Disorders: A 10-Year Retrospective Study in Singapore", International Journal of Dermatology, vol. 32, No. 9, pp. 686-689, 1993.

Shanahan, "Pathogenesis of Ulcerative Colitis", The Lancet, vol. 342, pp. 407-411, 1993.
Shaw et al. (1986) "Two Antigen-Independent Adhesion Pathways Used By Human Cytotoxic T-Cell Clones" Nature 323:262-264.
Shaw, et al., "Cyclosporin A and Vitamin D Metabolism: Studies in Patients with Psoriasis and in Rats", Clinical Science, vol. 86, pp. 627-632, 1994.
Shaw, S. and G. E. Ginther Luce, "The Lymphocyte Function-Associated Antigen (LFA)-1 and CD2/LFA-3 Pathways of Antigen-Independent Human T Cell Adhesion," J. Immunol., 139, pp. 1037-1045 (Aug. 15, 1987).
Shimizu, et al "Four Molecular Pathways of T Cell Adhesion to Endothelial Cells: roles of :FA-1, VCAM-1 and ELAM-1 and Changes in Pathway Hierarchy Under Different Activation Conditions", J. Cell. Biol. 113(5):1203-1212 (1991).
Short, J. M., et al., ".lambda. ZAP: A Bacteriophage Expression Vector with In Vivo Excision Properties," Nucleic Acids Research, 16(15), pp. 7583-7600 (1988).
Shupak, "Maintenance Therapy with Neoral.RTM.", International Journal of Dermatology, vol. 36, pp. 34-36, 1997.
Simon et al. (1991) "Adhesion molecules CD11a, CD18, and ICAM-2 on Human Epidermal Langerhans Cells Serve a Functional Role in the Activation of Alloreactive T Cells" Soc. Invest. Dermat. 96(1): 148-151.
Singer et al. (1990) "Thymocyte LFA-1 And Thymic Epithelial Cell ICAM-1 Molecules Mediate Binding Of Activated Human Thymocytes To Thymic Epithelial Cells" J. Immunol. 144(8):2931-2939.
Singer, K.H. et al. "The Role of Adhesion Molecules in Epithelial—T-Cell Interactions in Thymus and Skin", J. Invest. Dermatol. 94 (6) Supplement: 85S-90S.
Singh, et al., "Acute Immobilization Stress Triggers Skin Last Cell Degranulation via Corticotropin Releasing Hormone, Neurotensin, and Substance P: A Link to Neurogenic Skin Disorders", Brain Behavior, and Immunity, vol. 13, pp. 225-239, 1999.
Smith, et al. (1990) "Cellular Expression Of Lymphocyte Function Associated Antigens And The Intercellular Adhesion Molecule-1 In Normal Tissue" J. Olin. Path. 43 (11):893-900.
Smith, and Barker, "Cell Trafficking and Role of Adhesion Molecules in Psoriasis", Clinics in Dermatology, vol. 13, pp. 151-160, 1995.
Sofer and Britton "Designing an Optimal Chromatographic Purification Scheme for Proteins" Bio/Techniques 1(4):198-203 (1983).
Somerville, and Scott, "Neoral-New Cyclosporin For Old?", British Journal of Rheumatology, vol. 36, pp. 1113-1115, 1997.
Southern, E. M. "Detection of Specific Sequences Among DNA Fragments Separated by Gel Electrophoresis", J. Mol. Biol., 98, 503-517 (1975).
Spadaro, et al., "Comparison of cyclosporine A and methotrexate in the treatment of psoriatic arthritis: a one-year prospective study", Olin. Exp. Rheum. 13:589-593 (1995).
Springer "Adhesion Receptors Of The Immune System" Nature 346:425-434.
Springer (1987) "The Lymphocyte Function-Associated LFA-1, CD2, And LFA-3 Molecules: Cell Adhesion Receptors Of The Immune System" Ann. Rev. Immunol. 5:223-252.
Spuls et al., "A Systematic Review of Five Systematic Treatments for Severe Psoriasis", British Journal of Dermatology, vol. 137, pp. 943-949, 1997.
Srinivasachar, K. and D. M. Neville, Jr., "New Protein Cross-Linked Reagents That Are Cleaved by Mild Acid," Biochemistry, 28(4), pp. 2501-2509 (1989).
Staunton et al. (1989) "Molecular characterization of ICAM-1 and ICAM-2; Alternate Ligands for LFA-1" Tissue Antigens 33:287 (Abstract).
Stedman's Medical Dictionary, (1976) The Williams & Wilkins Company, .Baltimore, MD, p. 810.
Stern, "Narrowband UV-B and Psoriasis", Arch Dermatol, vol. 133, pp. 1587-1588, 1997.
Stern, "Psoriasis", The Lancet, vol. 350, pp. 349-353, 1997.
Stern, "Utilization of Outpatient Care for Psoriasis", Journal of the American Academy of Dermatology, vol. 35, No. 4, pp. 543-549, 1996.

Stern, et al., "Malignant Melanoma in Patients Treated for Psoriasis with Methoxsalen (Psoralen) and Ultraviolet A Radiation (PUVA)", The New England Journal of Medicine, vol. 336, No. 15, pp. 1041-1045, 1997.

Stern, et al., "The Safety of Etretinate as Long-Term Therapy for Psoriasis: Results of the Etretinate Follow-Up Study", Journal of the American Academy of Dermatology, vol. 33, No. 1, pp. 44-52, 1995.

Storkus, and Dawson, "A Target Structures Involved in Natural Killing (NK): Characteristics, Distribution, and Candidate Molecules", Immunology, vol. 10, No. 5, 393-416, 1991.

Strand, "The Future Use of Biologic Therapies in Combination for the Treatment of Rheumatoid Arthritis", J. Rhematol. 23 (suppl. 44):91-96 (1996).

Sultan, et al., "Blockade of CD2-LFA-3 Interactions Protects Human Skin Allografts in Immunodeficient Mouse/Human Chimeras", Nature Biotechnology, vol. 15, pp. 759-762, 1997.

Suranji et al. (1991) "Lymphocyte Adhesion Molecules in T Cell-Mediated Lysis of Human Kidney Cells" Kidney International 39:312-319.

Sutherland, et al., "Standards for Trials of Therapy in Inflammatory Bowel Disease", Inflammatory Bowel Diseases, vol. 3, No. 4, pp. 277-283, 1997.

Tadini (1989) "Adhesion Molecules Expression in Psoriasis" J. Invest. Dermatol. 93(2):309A (Abstract).

Talwar, et al., "Sequential Clinico-Histological Studies in Psoriasis Following Methotrexate Therapy", Ind J Dermatol Venereol Leprol, vol. 61, pp. 284-287, 1995.

Tand and Udey (1991) "Inhibition of Epidermal Langerhans Cell Function by Low Dose of Ultraviolet B Radiation" J. lmmunol. 146(10):3347-3355.

Task Force of the Working Group on Arrhythmias of the European Society of Cardiology, "The Early Termination of Clinical Trials: Causes, Consequences, and Control", European Heart Journal, vol. 15, pp. 721-738, 1994.

The Merck Manual of Diagnosis and Therapy Sixteenth Edition Edited by Berkow et al., Merck Research Laboratories, Rahway NJ 1992, pp. 2435-2445.

Thomas, et al., "Transdermal Nicotine as Maintenance Therapy for Ulcerative Colitis", The New England Journal of Medicine, vol. 332, No. 15, pp. 988-992, 1995.

Thomas, et al., "Purification of Membrane Proteins" in Methods in Enzymology, Deutscher, M. ed., (Academic Press, San Diego) 182: 499 (1990) (cited for argument).

Ticho, et al., "Reduced T cell monitoring in psoriasis patients receiving alefacept: results of clinical studies and mathematical modeling", J. Inves. Derm. 124(4): A40 (2005) (Abstract).

Traunecker et al., "A novel approach for preparing anti-T cell receptor constant region antibodies", 1986, Eur. J. Immunol., vol. 16;851-854.

Traunecker et al., "Soluble CD4 molecules neutralize human immunodeficiency virus type 1", 1988, Nature, vol. 331;84-86.

Traupe, "The Puzzling Genetics of Psoriasis", Clinics in Dermatology, vol. 13, pp. 99-103, 1995.

Trembath, et al., "Identification of a Major Susceptibility Locus on Chromosome 6p and Evidence for Further Disease Loci Revealed by a Two Stage Genome-Wide Search in Psoriasis", Human Molecular Genetics, vol. 6, No. 5, pp. 813-820, 1997.

Uchio, et al., "Suppression of Experimental Uveitis With Monoclonal Antibodies to ICAM-1 and LFA-1", Invest. Opthamol. Vis. Sci. 35(5):2626-2631 (1994).

Ullman et al. (1990) "Transmission of Signals from T Lymphocyte Antigen Receptor to the Genes Responsible for Cell Proliferation and Immune Function: The Missing Link" Ann. Rev. Immunol. 8:421-452.

Urlaub, and Chasin, "Isolation of Chinese Hamster Cell Mutants Deficient in Dihydrofolate Reductase Activity", Proc Natl Acad Sci, vol. 77, No. 7, pp. 4216-4220, 1980.

Urlaub, et al., "Effect of Gamma Rays at the Dihydrofolate Reductase Locus: Deletions and Inversions", Somatic Cell and Molecular Genetics, vol. 12, No. 6, pp. 555-566, 1986.

Valdimarsson et al. (1986) "Psoriasis: a disease of abnormal keratinoctye proliferation induced by T lymphocytes" Immunol. Today 7:256-259.

Valdimarsson, et al., "Psoriasis: A T-Cell-Mediated Autoimmune Disease Induced by Streptococcal Superantigens?", Immunology Today, vol. 16, No. 3, pp. 145-149, 1995.

Van De Kerkhof, "An Update on Vitamin D3 Analogues in the Treatment of Psoriasis", Skin Pharmacology and Applied Skin Physiology, vol. 11, pp. 2-10, 1998.

Van De Kerkhof, "Reduction of Epidermal Abnormalities and Inflammatory Changes in Psoriatic Plaques During Treatment with Vitamin D3 Analogs", Journal of Investigative Dermatology Symposium Proceedings, vol. 1, pp. 78-81, 1996.

Van De Kerkhof, "Review: The Management of Psoriasis", Netherlands Journal of Medicine, vol. 52, pp. 40-45, 1998.

Van De Kerkhof, "The Psoriasis Area and Severity Index and Alternative Approaches for the Assessment of Severity: Persisting Areas of Confusion", British Journal of Dermatology, vol. 137, pp. 661-662, 1997.

Vand De Kerkhof, et al., "Evaluation of Topical Drug Treatment in Psoriasis", Dermatology, vol. 197, pp. 31-36, 1998.

Van De Kerkhof, et al., "TheEffect of Addition of Calcipotriol Ointment (50 .mu.g/g) to Acitretin Therapy in Psoriasis", British Journal of Dermatology, vol. 138, pp. 84-89, 1998.

Van Der Merve, et al., "Human Cell-Adhesion Molecule CD2 Binds CD58 (LFA-3) with a Very Low Affinity and an Extremely Fast Dissociation Rate but does not Bind CD48 or CD59", Biochemistry, vol. 33, pp. 10149-10160, 1994.

Van Der Rhee, et al., "Combined Treatment of Psoriasis with a New Aromatic Retinoid (Tigason) in Low Dosage Orally and Triamcinolone Acetonide Cream Topically: A Double-Blind Trial", British Journal of Dermatology, vol. 102, pp. 203-211, 1980.

Van Kooyk, et al., "Enhancement of LFA-1-Mediated Cell Adhesion by Triggering through CD2 or CD3 on T Lymphocytes", Nature, vol. 342, pp. 811-813, 1989.

Van Nort, et al., "Cell Biology of Autoimmune Diseases", in International Review of Cytology: A Survey of Cell Biology, Jeon, K. ed. (Academic Press, San Diego, 1998), pp. 127-207.

Van Onselen, "Psoriasis in General Practice", Nursing Standard, vol. 12, No. 30, pp. 32-33, 1998.

Van Seventer et al. (1989) "The Three LFA-3 Specific Monoclonal Antibodies in the Non-Lineage panel of Workshop Monoclonal Antibodies All Inhibit T-Cell Rosetting" Tissue Antigens 33:298 (Abstract).

Van Seventer, et al. "Roles of multiple accessory mulecules in T-cell activation", Curr. Opin. Immunol. 3(3):294-303 (1991).

Verhoeven, et al., "Combination Therapy in Rheumatoid Arthritis: Updated systematic review", Br. J. Rheum. 37:612-619(1998).

Verstuyf, et al., "Recent Developments in the Use of Vitamin D Analogues", Expert Opin Investig Drugs, vol. 9, No. 3, pp. 397-403, 1998.

Virella et al. (1988) "The Interaction of CD2 With Its LFA-3 Ligand Expressed By Autologous Erythrocytes Results in Enhancement of B Cell Responses" Cell. lmmunol. 116:308-319.

Vollger et al. (1987) "Thymocyte Binding To Human Tymic Epithelial Cells is Inhibited by Monoclonal Antibodies To CD-2 And LFA-3 Antigens" J. lmmunol. 138(2):358-363.

Wahl, "The Impact of Psoriasis on Psychosocial Life Domains: A Review", Scandinavian Journal of Caring Science, vol. 11, pp. 243-249, 1997.

Wahl, et al., "Sulfasalazine: A Potent and Specific Inhibitor of Nuclear Factor Kappa B", Journal of Clinical Investigation, vol. 101, No. 5, pp. 1163-1174, 1998.

Waldman (1991) "Monoclonal Antibodies in Diagnosis and Therapy" Science 252:1657-1662.

Wallner et al (1987) "Primary Structure of Lymphocyte Function-Associated Antigen 3 (LFA-3)—The Ligand of the Lymphocyte CD2 Glycoprotein" J. Exp. Med. 166(4):923-931.

Wallner, et al., "Cloning and Expression of Human Lipocortin, a Phospholipase A2 Inhibitor with Potential Anti-Inflammatory Activity", Nature, 320(6), 77-81 (1986).

Walters, et al., "Suberythemogenic narrow-band UVB is markedly more effective than conventional UVB in treatment of psoriasis vulgaris", J.Acad. Dermatol. 40(6) 893-900.

Wang, et al., "Structure of a Heterophilic Adhesion Complex between the Human CD2 and CD58 (LFA-3) Counterreceptors", Cell, vol. 97, pp. 971-803, 1999.

Wang, X. et al., "A Vector That Expresses Secreted Proteins on the Cell Surface," DNA, 8(10), pp. 753-758 (Dec. 1989).

Wanquinq, et al., "Clinical Study of Cyclosporin A for Psoriasis in China", Annals of Dermatology, vol. 7, No. 4, pp. 313-317, 1995.

Watanabe, et al., "Effect of recombinant soluble CD4 in rhesus monkeys infected with simian immunodeficiency virus of macaques", Nature 337:267(1989) (cited for argument).

Webb et al. (1990) "LFA-3, CD44, And CD45: Physiologic Triggers Of Human Monocyte TNF and IL-1 Release" Science 249:1295-1297.

Weinblatt, "Efficacy of Methotrexate in Rheumatoid Arthritis" Br. J. Rheum. 34(S2)43-48 (1995).

Weinblatt, et al., "Methotrexate for Chronic Diseases in Adults", The New England Journal of Medicine, vol. 332, No. 5, pp. 330-331, 1995.

Weinblatt, et al., "Efficacy of Methotrexate in Rheumatoid Arthritis", Br. J. Rheum. 34(Supp 2):43-48 (1995).

Weiner, et al., "Phase I Evaluation of an Anti-Breast Carcinoma Monoclonal Antibody 260F9-Recombinant Ricin A Chain Immunoconjugate", Cancer Research, vol. 49, pp. 4062-4067, 1989.

Weinstein, "Psoriasis Therapy After Remission: The Next Step", International Journal of Dermatology, vol. 36(Suppl 1), pp. 37-40, 1997.

Weinstein, "Tazarotene Gel: Efficacy and Safety in Plaque Psoriasis", Journal of the American Academy of Dermatology, vol. 37, No. 2, pp. S33-S38, 1997.

Weinstein, et al., "Tazarotene Gel, a New Retinoid, for Topical Therapy of Psoriasis: Vehicle-Controlled Study of Safety, Efficacy, and Duration of Therapeutic Effect", Journal of the American Academy of Dermatology, vol. 37, No. 1, pp. 85-92, 1997.

Weiss, and Ashwell, "The Asialoglycoprotein Receptor: Properties and Modulation by Ligand", Baumann, P., et al. (Ed.). Progress in Clinical and Biological Research, vol. 300.

Wendling, et al. "Therapeutic Use of Monoclonal Anti-CD4 Antibody in Rheumatoid Arthritis", J. Rheum. 18(3): 325-7 (1991) ) (abstract only).

Weyand, et al. "Immunosuppression by Anti-CD4 Treatments In Vivo", Transplantation 47(6):1039-1042 (1989).

Whitcup, et al., "Monoclonal Antibodies against ICAM-1 (CD54) and LFA-1 (CD11a/CD18) Inhibit Experimental Autoimmune Uveitis", Clin. Immunol Immunopathol 67(2):143-150 (1993).

Whitmore, and Morison, "Melanoma after PUVA Therapy for Psoriasis", The New England Journal of Medicine, vol. 337, No. 7, pp. 502, 1997.

Willkens, et al., "Randomized, Double-Blind, Placebo Controlled Trial of Low-Dose Pulse Methotrexate in Psoriatic Arthritis", Arthritis and Rheumatism, vol. 27, No. 4, pp. 376-381, 1984.

Winter and Harris (1993) "Humanized antibodies" TiPS 14(5):139-142.

Wolska, et al., "Etretinate in Severe Psoriasis: Results of Double-Blind Study and Maintenance Therapy in Pustular Psoriasis", Journal of the American Academy of Dermatology, vol. 9, No. 6, pp. 883-887, 1983.

Wong et al., "Identification of a Partial cDNA Clone for the Human Receptor for Completement Fragments C3b/C4b," Proc. Natl. Acad. Sci. U.S.A., 82, 7711-7715 (1985).

Wong, et al., "Mechanisms of action of cyclosporine A in the treatment of psoriasis", Immunol. Today 14(2):69-74 (1993).

Wood, W. I. (1987) "Gene Cloning Based on Long Oligoneucleotide Probes", Meth. Entymol. 152:443-47.

Wright, et al., "Human Low-Dosage Parenteral Methotrexate Therapy: A Controlled Toxicity Study", Arch Derm, vol. 93, pp. 731-736, 1966.

Written Opinion PCT/US02/02314.

Yamashita, et al., "A multimeric form of soluble recombinant sheep LFA-3 (CD-58) inhibits human T-cell proliferation" Immunol. 92(1):39-44 (1997).

Yeh, et al., "Recombinant Soluble Human Complement Receptor Type 1 Inhibits Inflammation in the Reversed Passive Arthus Reaction in Rats", J. Immunol. 146(1):250 (1991) (cited for argument).

Yocum, et al., "Clinical and immunological effects of a Primatized Anti-CD4 Monoclonal Antibody in Active Rheumatoid Arthritis: Results of a Phase I, Single Dose, Dose Escalating Trial", Journal of Rheumatology, vol. 25, pp. 1257-1262, 1998.

Yong and Khwaja (1990) "Leukocyte Cellular Adhesion Molecules" Blood Reviews 4(4):211-225.

Young, et al., "A Prospective study of Renal Structure and Function in Psoriasis Patients with Cyclosporin", Kidney International, vol. 46, pp. 1216-1222, 1994.

Zachariae, "Alcohol Interaction with Drugs and its Effects on the Treatment of Skin Diseases", Clinics in Dermatology, vol. 17, pp. 443-445, 1999.

Zettlmeissl, et al., "Expression and Characterization of Human CD4: Immunoglobulin Fusion Proteins", DNA & Cell Biol. 9(5):347-353 (1990).

Zheng et al. (1990) "Expression Of Intercellular Adhesion Molecule-1 And Lymphocyte Function-Associated Antigen-3 On Human Thyroid Epithelial Cells in Graves' and Hashimoto's Diseases" J. Autoimmunity 3:727-736.

Translation of Examiner's report for Czech Patent Application No. PV 2001-725.

European Patent Office, European Search Report for European Application No. 05713080.0 issued Aug. 8, 2008.

Gordon et al., Journal of the American Academy of Dermatology, V. 50, No. 3, Mar. 2004, p. 152 (Abstract).

Krueger et al., Journal of the American Academy of Dermatology, V. 47., No. 6, Dec. 2002, pp. 821-833.

Krueger et al., Journal of the American Academy of Dermatology, V. 50, No. 3, Mar. 2004, p. 152 (Abstract).

Lebwohl et al., Archives of Dermatology, V.139, No. 6, Jun. 1, 2003, pp. 719-727.

Lowe et al., International Journal of Dermatology, V. 42, No. 3, Mar. 2003, pp. 224-230.

Menter et al., Journal of the American Academy of Dermatology, V. 50, No. 3, Mar. 2005, p. 151 (Abstract).

Beers et al., Editors, Merck Manual of Diagnosis and Therapy, Seventeenth Edition, Merck Research Laboratories, Whitehouse Station, pp. 816-818 (1999) cited in C634 below.

BIOGEN IDEC, Safety Letter, Cambridge, MA (Oct. 2005).

CIPO, Official communication relative to co-pending Canadian Application No. 2,565,259 mailed Apr. 30, 2009.

CIPO Official communication relative to related Canadian Application No. 2,454,618 mailed May 1, 2009.

EPO, Official communication relative to co-pending European Application No. 05779311.9 mailed Jan. 29, 2008.

EPO, Official communication relative to related European Application No. 05779971.0 mailed Jul. 24, 2008.

EPO, Official communication relative to related European Application No. 02749865.8 mailed May 8, 2009.

Magilavy et al., Journal of Investigative Dermatology, 110(4): 682 (Abstract 1260), (Apr. 1998).

USPTO, Office Action in related U.S. Appl. No. 10/588,323 mailed Apr. 8, 2009.

* cited by examiner

LFA-3 signal sequence

```
  1 ATG GTT GCT GGG AGC GAC GCG GGG CGG GCC CTG GGG GTC CTC AGC GTG GTC TGC
  1▶Met Val Ala Gly Ser Asp Ala Gly Arg Ala Leu Gly Val Leu Ser Val Val Cys

55 CTG CTG CAC TGC TTT GGT TTC ATC AGC TGT
 19▶Leu Leu His Cys Phe Gly Phe Ile Ser Cys
```

LFA-3

```
 85 TTT TCC CAA CAA ATA TAT GGT GTT GTG TAT GGG AAT GTA ACT TTC CAT GTA CCA
 29▶Phe Ser Gln Gln Ile Tyr Gly Val Val Tyr Gly Asn Val Thr Phe His Val Pro

139 AGC AAT GTG CCT TTA AAA GAG GTC CTA TGG AAA AAA CAA AAG GAT AAA GTT GCA
 47▶Ser Asn Val Pro Leu Lys Glu Val Leu Trp Lys Lys Gln Lys Asp Lys Val Ala

193 GAA CTG GAA AAT TCT GAA TTC AGA GCT TTC TCA TCT TTT AAA AAT AGG GTT TAT
 65▶Glu Leu Glu Asn Ser Glu Phe Arg Ala Phe Ser Ser Phe Lys Asn Arg Val Tyr

247 TTA GAC ACT GTG TCA GGT AGC CTC ACT ATC TAC AAC TTA ACA TCA TCA GAT GAA
 83▶Leu Asp Thr Val Ser Gly Ser Leu Thr Ile Tyr Asn Leu Thr Ser Ser Asp Glu

301 GAT GAG TAT GAA ATG GAA TCG CCA AAT ATT ACT GAT ACC ATG AAG TTC TTT CTT
101▶Asp Glu Tyr Glu Met Glu Ser Pro Asn Ile Thr Asp Thr Met Lys Phe Phe Leu

355 TAT GTC
119▶Tyr Val
```

IgG1 (hinge, CH2, CH3)

```
361 GAC AAA ACT CAC ACA TGC CCA CCG TGC CCA GCA CCT GAA CTC CTG GGG GGA CCG
121▶Asp Lys Thr His Thr Cys Pro Pro Cys Pro Ala Pro Glu Leu Leu Gly Gly Pro

415 TCA GTC TTC CTC TTC CCC CCA AAA CCC AAG GAC ACC CTC ATG ATC TCC CGG ACC
139▶Ser Val Phe Leu Phe Pro Pro Lys Pro Lys Asp Thr Leu Met Ile Ser Arg Thr

469 CCT GAG GTC ACA TGC GTG GTG GTG GAC GTG AGC CAC GAA GAC CCT GAG GTC AAG
157▶Pro Glu Val Thr Cys Val Val Val Asp Val Ser His Glu Asp Pro Glu Val Lys

523 TTC AAC TGG TAC GTG GAC GGC GTG GAG GTG CAT AAT GCC AAG ACA AAG CCG CGG
175▶Phe Asn Trp Tyr Val Asp Gly Val Glu Val His Asn Ala Lys Thr Lys Pro Arg

577 GAG GAG CAG TAC AAC AGC ACG TAC CGT GTG GTC AGC GTC CTC ACC GTC CTG CAC
193▶Glu Glu Gln Tyr Asn Ser Thr Tyr Arg Val Val Ser Val Leu Thr Val Leu His

631 CAG GAC TGG CTG AAT GGC AAG GAG TAC AAG TGC AAG GTC TCC AAC AAA GCC CTC
211▶Gln Asp Trp Leu Asn Gly Lys Glu Tyr Lys Cys Lys Val Ser Asn Lys Ala Leu

685 CCA GCC CCC ATC GAG AAA ACC ATC TCC AAA GCC AAA GGG CAG CCC CGA GAA CCA
229▶Pro Ala Pro Ile Glu Lys Thr Ile Ser Lys Ala Lys Gly Gln Pro Arg Glu Pro

739 CAG GTG TAC ACC CTG CCC CCA TCC CGG GAT GAG CTG ACC AAG AAC CAG GTC AGC
247▶Gln Val Tyr Thr Leu Pro Pro Ser Arg Asp Glu Leu Thr Lys Asn Gln Val Ser

793 CTG ACC TGC CTG GTC AAA GGC TTC TAT CCC AGC GAC ATC GCC GTG GAG TGG GAG
265▶Leu Thr Cys Leu Val Lys Gly Phe Tyr Pro Ser Asp Ile Ala Val Glu Trp Glu

847 AGC AAT GGG CAG CCG GAG AAC AAC TAC AAG ACC ACG CCT CCC GTG TTG GAC TCC
283▶Ser Asn Gly Gln Pro Glu Asn Asn Tyr Lys Thr Thr Pro Pro Val Leu Asp Ser

901 GAC GGC TCC TTC TTC CTC TAC AGC AAG CTC ACC GTG GAC AAG AGC AGG TGG CAG
301▶Asp Gly Ser Phe Phe Leu Tyr Ser Lys Leu Thr Val Asp Lys Ser Arg Trp Gln

955 CAG GGG AAC GTC TTC TCA TGC TCC GTG ATG CAT GAG GCT CTG CAC AAC CAC TAC
319▶Gln Gly Asn Val Phe Ser Cys Ser Val Met His Glu Ala Leu His Asn His Tyr

1009 ACG CAG AAG AGC CTC TCC CTG TCT CCG GGT AAA TGA
337▶Thr Gln Lys Ser Leu Ser Leu Ser Pro Gly Lys •••
```

FIG. 1A

SEQUENCE LISTING

```
<160> NUMBER OF SEQ ID NOS: 4

<210> SEQ ID NO 1
<211> LENGTH: 753
<212> TYPE: DNA
<213> ORGANISM: Homo sapiens
<220> FEATURE:
<221> NAME/KEY: misc_feature
<222> LOCATION: (1)..(750)
<223> OTHER INFORMATION: CDS
<220> FEATURE:
<221> NAME/KEY: sig_peptide
<222> LOCATION: (1)..(84)
<220> FEATURE:
<221> NAME/KEY: misc_feature
<222> LOCATION: (1)..(750)
<223> OTHER INFORMATION: Human transmembrane LFA-3
<220> FEATURE:
<221> NAME/KEY: misc_feature
<222> LOCATION: (85)..(750)
<223> OTHER INFORMATION: mat_peptide
<220> FEATURE:
<221> NAME/KEY: misc_feature
<222> LOCATION: (646)..(0)
<223> OTHER INFORMATION: Transmembrance domain

<400> SEQUENCE: 1
atggttgctg ggagcgacgc ggggcgggcc ctggggtcc tcagcgtggt ctgcctgctg      60
cactgctttg gtttcatcag ctgttttcc caacaaatat atggtgttgt gtatgggaat     120
gtaactttcc atgtaccaag caatgtgcct ttaaaagagg tcctatggaa aaaacaaaag     180
gataaagttg cagaactgga aaattctgaa ttcagagctt tctcatcttt taaaaatagg     240
gtttatttag acactgtgtc aggtagcctc actatctaca acttaacatc atcagatgaa     300
gatgagtatg aaatggaatc gccaaatatt actgatacca tgaagttctt tctttatgtg     360
cttgagtctc ttccatctcc cacactaact tgtgcattga ctaatggaag cattgaagtc     420
caatgcatga taccagagca ttacaacagc catcgaggac ttataatgta ctcatgggat     480
tgtcctatgg agcaatgtaa acgtaactca accagtatat attttaagat ggaaaatgat     540
cttccacaaa aaatacagtg tactcttagc aatccattat taatacaac atcatcaatc     600 attttgacaa cctgtatccc aagcagcggt cattcaagac acagatatgc acttataccc     660
ataccattag cagtaattac aacatgtatt gtgctgtata tgaatggtat tctgaaatgt     720
gacagaaaac cagacagaac caactccaat tga                                  753
```

```
<210> SEQ ID NO 2
<211> LENGTH: 250
<212> TYPE: PRT
<213> ORGANISM: Homo sapiens

<400> SEQUENCE: 2

Met Val Ala Gly Ser Asp Ala Gly Arg Ala Leu Gly Val Leu Ser Val
1               5                   10                  15

Val Cys Leu Leu His Cys Phe Gly Phe Ile Ser Cys Phe Ser Gln Gln
            20                  25                  30

Ile Tyr Gly Val Val Tyr Gly Asn Val Thr Phe His Val Pro Ser Asn
        35                  40                  45

Val Pro Leu Lys Glu Val Leu Trp Lys Lys Gln Lys Asp Lys Val Ala
50                  55                  60

Glu Leu Glu Asn Ser Glu Phe Arg Ala Phe Ser Ser Phe Lys Asn Arg
65                  70                  75                  80

Val Tyr Leu Asp Thr Val Ser Gly Ser Leu Thr Ile Tyr Asn Leu Thr
                85                  90                  95

Ser Ser Asp Glu Asp Glu Tyr Glu Met Glu Ser Pro Asn Ile Thr Asp
            100                 105                 110

Thr Met Lys Phe Phe Leu Tyr Val Leu Glu Ser Leu Pro Ser Pro Thr
        115                 120                 125

Leu Thr Cys Ala Leu Thr Asn Gly Ser Ile Glu Val Gln Cys Met Ile
    130                 135                 140

Pro Glu His Tyr Asn Ser His Arg Gly Leu Ile Met Tyr Ser Trp Asp
145                 150                 155                 160

Cys Pro Met Glu Gln Cys Lys Arg Asn Ser Thr Ser Ile Tyr Phe Lys
                165                 170                 175

Met Glu Asn Asp Leu Pro Gln Lys Ile Gln Cys Thr Leu Ser Asn Pro
            180                 185                 190

Leu Phe Asn Thr Thr Ser Ser Ile Ile Leu Thr Thr Cys Ile Pro Ser
        195                 200                 205

Ser Gly His Ser Arg His Arg Tyr Ala Leu Ile Pro Ile Pro Leu Ala
    210                 215                 220

Val Ile Thr Thr Cys Ile Val Leu Tyr Met Asn Gly Ile Leu Lys Cys
225                 230                 235                 240

Asp Arg Lys Pro Asp Arg Thr Asn Ser Asn
                245                 250

<210> SEQ ID NO 3
<211> LENGTH: 1050
<212> TYPE: DNA
<213> ORGANISM: Homo sapiens
<220> FEATURE:
<221> NAME/KEY: CDS
<222> LOCATION: (1)..(1050)

<400> SEQUENCE: 3 atg gtt gct ggg agc gac gcg ggg ctg ggg cgg gcc ctg ggg gtc ctc      48
Met Val Ala Gly Ser Asp Ala Gly Leu Gly Arg Ala Leu Gly Val Leu
1               5                   10                  15 agc gtg gtc tgc ctg ctg cac tgc ttt ggt ttc atc agc tgt ttt tcc      96
Ser Val Val Cys Leu Leu His Cys Phe Gly Phe Ile Ser Cys Phe Ser
            20                  25                  30 caa caa ata tat ggt gtt gtg tat ggg aat gta act ttc cat gta cca     144
Gln Gln Ile Tyr Gly Val Val Tyr Gly Asn Val Thr Phe His Val Pro
        35                  40                  45 agc aat gtg cct tta aaa gag gtc cta tgg aaa aaa caa aag gat aaa     192
```

```
Ser Asn Val Pro Leu Lys Glu Val Leu Trp Lys Lys Gln Lys Asp Lys
    50                  55                  60 gtt gca gaa ctg gaa aat tct gaa ttc aga gct ttc tca tct ttt aaa          240
Val Ala Glu Leu Glu Asn Ser Glu Phe Arg Ala Phe Ser Ser Phe Lys
 65                  70                  75                  80 aat agg gtt tat tta gac act gtg tca ggt agc ctc act atc tac aac          288
Asn Arg Val Tyr Leu Asp Thr Val Ser Gly Ser Leu Thr Ile Tyr Asn
                     85                  90                  95 tta aca tca tca gat gaa gat gag tat gaa atg gaa tcg cca aat att          336
Leu Thr Ser Ser Asp Glu Asp Glu Tyr Glu Met Glu Ser Pro Asn Ile
                100                 105                 110 act gat acc atg aag ttc ttt ctt tat gtc gac aaa act cac aca tgc          384
Thr Asp Thr Met Lys Phe Phe Leu Tyr Val Asp Lys Thr His Thr Cys
            115                 120                 125 cca ccg tgc cca gca cct gaa ctc ctg ggg gga ccg tca gtc ttc ctc          432
Pro Pro Cys Pro Ala Pro Glu Leu Leu Gly Gly Pro Ser Val Phe Leu
130                 135                 140 ttc ccc cca aaa ccc aag gac acc ctc atg atc tcc cgg acc cct gag          480
Phe Pro Pro Lys Pro Lys Asp Thr Leu Met Ile Ser Arg Thr Pro Glu
145                 150                 155                 160 gtc aca tgc gtg gtg gtg gac gtg agc cac gaa gac cct gag gtc aag          528
Val Thr Cys Val Val Val Asp Val Ser His Glu Asp Pro Glu Val Lys
                    165                 170                 175 ttc aac tgg tac gtg gac ggc gtg gag gtg cat aat gcc aag aca aag          576
Phe Asn Trp Tyr Val Asp Gly Val Glu Val His Asn Ala Lys Thr Lys
                180                 185                 190 ccg cgg gag gag cag tac aac agc acg tac cgg gtg gtc agc gtc ctc          624
Pro Arg Glu Glu Gln Tyr Asn Ser Thr Tyr Arg Val Val Ser Val Leu
            195                 200                 205 acc gtc ctg cac cag gac tgg ctg aat ggc aag gag tac aag tgc aag          672
Thr Val Leu His Gln Asp Trp Leu Asn Gly Lys Glu Tyr Lys Cys Lys
210                 215                 220 gtc tcc aac aaa gcc ctc cca gcc ccc atc gag aaa acc atc tcc aaa          720
Val Ser Asn Lys Ala Leu Pro Ala Pro Ile Glu Lys Thr Ile Ser Lys
225                 230                 235                 240 gcc aaa ggg cag gcc cga gaa cca cag gtg tac acc ctg ccc cca tcc          768
Ala Lys Gly Gln Ala Arg Glu Pro Gln Val Tyr Thr Leu Pro Pro Ser
                    245                 250                 255 cgg gat gag ctg acc aag aac cag gtc agc ctg acc tgc ctg gtc aaa          816
Arg Asp Glu Leu Thr Lys Asn Gln Val Ser Leu Thr Cys Leu Val Lys
                260                 265                 270 ggc ttc tat ccc agc gac atc gcc gtg gag tgg gag agc aat ggg cag          864
Gly Phe Tyr Pro Ser Asp Ile Ala Val Glu Trp Glu Ser Asn Gly Gln
            275                 280                 285 ccg gag aac aac tac aag acc acg cct ccc gtg ctg gac tcc gac ggc          912
Pro Glu Asn Asn Tyr Lys Thr Thr Pro Pro Val Leu Asp Ser Asp Gly
290                 295                 300 tcc ttc ttc ctc tac agc aag ctc acc gtg gac aag agc agg tgg cag          960
Ser Phe Phe Leu Tyr Ser Lys Leu Thr Val Asp Lys Ser Arg Trp Gln
305                 310                 315                 320 cag ggg aac gtc ttc tca tgc tcc gtg atg cat gag gct ctg cac aac         1008
Gln Gly Asn Val Phe Ser Cys Ser Val Met His Glu Ala Leu His Asn
                    325                 330                 335 cac tac acg cag aag agc ctc tcc ctg tct ccg ggt aaa tga                 1050
His Tyr Thr Gln Lys Ser Leu Ser Leu Ser Pro Gly Lys
                340                 345

<210> SEQ ID NO 4
<211> LENGTH: 349
<212> TYPE: PRT
```

-continued

```
<213> ORGANISM: Homo sapiens

<400> SEQUENCE: 4

Met Val Ala Gly Ser Asp Ala Gly Leu Gly Arg Ala Leu Gly Val Leu
1               5                   10                  15

Ser Val Val Cys Leu Leu His Cys Phe Gly Phe Ile Ser Cys Phe Ser
                20                  25                  30

Gln Gln Ile Tyr Gly Val Val Tyr Gly Asn Val Thr Phe His Val Pro
            35                  40                  45

Ser Asn Val Pro Leu Lys Glu Val Leu Trp Lys Lys Gln Lys Asp Lys
        50                  55                  60

Val Ala Glu Leu Glu Asn Ser Glu Phe Arg Ala Phe Ser Ser Phe Lys
65                  70                  75                  80

Asn Arg Val Tyr Leu Asp Thr Val Ser Gly Ser Leu Thr Ile Tyr Asn
                85                  90                  95

Leu Thr Ser Ser Asp Glu Asp Glu Tyr Glu Met Glu Ser Pro Asn Ile
                100                 105                 110

Thr Asp Thr Met Lys Phe Phe Leu Tyr Val Asp Lys Thr His Thr Cys
            115                 120                 125

Pro Pro Cys Pro Ala Pro Glu Leu Leu Gly Gly Pro Ser Val Phe Leu
        130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
                180                 185                 190

Pro Arg Glu Glu Gln Tyr Asn Ser Thr Tyr Arg Val Val Ser Val Leu
            195                 200                 205

Thr Val Leu His Gln Asp Trp Leu Asn Gly Lys Glu Tyr Lys Cys Lys
        210                 215                 220

Val Ser Asn Lys Ala Leu Pro Ala Pro Ile Glu Lys Thr Ile Ser Lys
225                 230                 235                 240

Ala Lys Gly Gln Ala Arg Glu Pro Gln Val Tyr Thr Leu Pro Pro Ser
                245                 250                 255

Arg Asp Glu Leu Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys
            340                 345
```

METHODS OF TREATING VIRAL DISORDERS

RELATED APPLICATIONS

This application claims the benefit of U.S. provisional application 60/568,955 filed May 7, 2004, the entire contents of which are hereby incorporated by reference herein.

BACKGROUND

Viral diseases are an increasing worldwide health concern.

HIV infection has been implicated as the primary cause of acquired immune deficiency syndrome (AIDS). Barre-Sinoussi et al. (1983) *Science* 220:868-870; and Gallo et al. (1984) *Science* 224:500-503. Infection of the CD4+ subclass of T-lymphocytes with the HIV-1 virus leads to depletion of this essential lymphocyte subclass which inevitably leads to opportunistic infections, neurological disease, neoplastic growth and eventually death. Anti-retroviral drugs, such as reverse transcriptase inhibitors, viral protease inhibitors, and viral entry inhibitors, have been used to treat HIV infection (Caliendo et al. (1994) Clin. Infect. Dis. 18:516-524). More recently, treatment with combinations of these agents, known as highly active antiretroviral therapy (HAART), has been used to suppress replication of HIV (Gulick et al. (1997) N. Engl. J. Med. 337:734-9 (see comments); Hammer et al. (1997) N. Engl. S. Med. 337:725-733). Viral hepatitis is a cause of considerable morbidity and mortality in the human population, both from acute infection and chronic sequelae which include, in the case of hepatitis B, C and D, chronic active hepatitis and cirrhosis. Promising classes of treatment agents for hepatitis include interferons (hepatitis B) and protease inhibitors (hepatitis C).

SUMMARY OF THE INVENTION

The invention provides methods and compositions for treating a subject who has a viral infection, e.g., a viral infection mediated, at least in part, by memory T-cells, e.g., human immunodeficiency virus (HIV) (e.g., HIV-1 or HIV-2); hepatitis virus, e.g., hepatitis C (HCV), hepatitis B (HBV), or hepatitis D (HDV); human T lymphotropic virus (HTLV, e.g., HTLV-1 or HILV-2); herpesvirus, e.g., Epstein-Barr virus (EBV), cytomegalovirus (CMV), herpes simplex type 1 (HSV-1), herpes simplex type 2 (HSV-2), herpes zoster virus (HZV), herpes virus type 6 (HHV-6), herpes virus type 7 (HHV-7), papillomavirus. The methods and compositions described herein relate to the administration of an inhibitor of the LFA-3/CD2 interaction, e.g., a soluble LFA-3 polypeptide, e.g., a soluble LFA-3-immunoglubulin (Ig) fusion protein such as AMVIVE® (alefacept) (hereinafter AMEEVIVE).

Accordingly, in one aspect, the invention features a method of treating a subject who is infected with a pathogenic virus. The method includes administering a soluble, CD2-binding LFA-3 polypeptide to the subject.

In a preferred embodiment, the subject is HIV-positive. The HIV-positive subject may or may not have AIDS, but preferably does not yet have AIDS. In some cases, the subject is or has been treated with retroviral therapy, e.g., combination therapy such as highly active retroviral therapy (HAART). In some embodiments, the subject has CD4 counts of at least above 200 cells/TL, e.g., at least above 300, 400, 500 or 1000 cells/TL.

In another preferred embodiment, the subject has positive hepatitis titres, e.g., HBV or HCV titres.

In preferred embodiments, the treatment is effective to reduce viral load (e.g., by at least 50%, preferably by at least one log, 2 logs, 3 logs or more), increase CD4+ count, and/or decrease CD45RO+ count.

Preferably, the soluble, CD2-binding LFA-3 polypeptide is an LFA-3 fusion protein, e.g., an LFA-3/immunoglobulin (Ig) fusion protein. An exemplary LFA-3/Ig fusion protein includes a soluble, CD2 binding LFA-3 polypeptide fused to all or part of an Fc region of an IgG, e.g., fused to all or part of an IgG heavy chain hinge region and all or part of a heavy chain constant region. In a preferred embodiment, the Ig fusion protein consists of the amino terminal 92 amino acids of mature LFA-3, the C-terminal 10 amino acids of a human IgG1 hinge region, a CH2 region of a human IgG1 heavy chain, and all or at least part of a CH3 region of a human IgG1 heavy chain. One such fusion protein is AMEVIVE. AMEVIVE is encoded by an insert contained in plasmid pSAB152, deposited with American Type Culture Collection, Manassas, Va. under the accession number ATCC 68720. AMEVIVE is described in more detail herein below.

The soluble, CD2 binding LFA-3 polypeptide can be administered at a dosage ranging from about 0.001 to about 50 mg binding agent per kg body weight. In one embodiment, the polypeptide is administered systemically, preferably by intramuscular (IM) or intravenous (IV) route. The administration period typically includes periodic administration of the polypeptide, e.g., once a week, twice a week, semi-weekly, or monthly. The polypeptide is typically administered at a unit dosage ranging from 2 to 15 mg when administered by IV route (for example, 7.5 mg IV bolus) and a unit dosage ranging from 2 to 30 mg when administered by IM route (for example, 15 mg IM injection).

In one embodiment, the method includes evaluating the subject for T cell status, e.g., evaluating the CD4+ and/or CD45RO+ status and/or cell count of the subject. In another embodiment, the method includes evaluating the subject for number or frequency of HIV-infected cells (HIV infected cells which may be either actively replicating or latent). The evaluation may be performed before, during and/or after the administration.

In one embodiment, the method includes administering to the subject (e.g., an HIV+ subject) an additional therapeutic or prophylactic agent during a course of treatment with the soluble, CD2-binding LFA-3 polypeptide. The additional agent is preferably not vitamin B12 or IL-15. The additional agent can be e.g., a protease inhibitor, e.g., Agenerase (amprenavir), Viracept (nelfinavir), Crixivan (indinavir), Reyataz (atazanavir; BMS-232632), Norvir (ritonavir), Lexiva (Fosamprenavir), Kaletra (lopinavir), Invirase (saquinavir), Fortovase (saquinavir); a reverse transcriptase inhibitor, e.g., Retrovir, AZT (zidovudine), Rescriptor (delavirdine), Sustiva (efavirenz), Ziagen (abacavir), Zerit (d4t/stavudine), Viread (tenofovir disoproxil fumarate), Viramune (nevirapine), Videx (ddI/didanosine); Emtriva [emtricitabine (FTC)], Fuzeon (enfuvirtide), or combinations of any of the foregoing, e.g., HAART. The additional agent can be administered before, during, and /or after the soluble, CD2-binding LFA-3 polypeptide.

The subject is preferably a human. Preferred subjects include those who have symptoms of a viral infection, e.g., a viral infection described herein, e.g., HIV or HCV, and those who have been diagnosed with HIV/AIDS. In one embodiment, the subject is co-infected with two or more viruses. For example, the subject is co-infected with HIV and a hepatitis virus (e.g., Hepatitis A, B or C) or a lymphotropic virus (e.g., HTLV-2).

BRIEF DESCRIPTION OF THE DRAWINGS

FIG. 1A depicts the amino acid (SEQ ID NO:3) and nucleotide (SEQ ID NO:4) sequence of an LFA-3/IgG fusion protein. The signal peptide corresponds to amino acids 1-28 of FIG. 1A; the mature LFA-3 region corresponds to amino acids 29-120 of FIG. 1A; and the IgG1 region corresponds to amino acids 121-347 of FIG. 1A.

DETAILED DESCRIPTION

The methods described herein relate generally to the treatment of subjects having a T cell mediated viral infection, e.g., HIV infection or HCV infection, with a soluble, CD2 binding LFA-3 polypeptide. The epidemiology, pathogenesis, diagnosis and current treatments of viral disease, including HIV/AIDS, hepatitis viruses, herepesviruses, papillomaviruses, and others are discussed, e.g., in *Viral Infections and Treatment* (*Infectious Disease and Therapy,* 30), Rubsamen-Waigmann et al., Eds., Marcel Dekker (2003); and *Viral Hepatitis: Diagnosis, Treatment, Prevention,* Richard Wilson, Ed. Marcel Dekker (1997).

Inhibitors of the CD2:LFA-3 Interaction

Any inhibitor of the CD2:LFA-3 interaction is useful in the methods of this invention. Such inhibitors include soluble LFA-3 polypeptides, anti-LFA-3 antibody homologs, anti-CD2 antibody homologs, soluble CD2 polypeptides, small molecules (e.g., a chemical agent having a molecular weight of less than 2500 Da, preferably, less than 1500 Da, a chemical, e.g., a small organic molecule, e.g., a product of a combinatorial library), LFA-3 and CD2 mimetic agents and derivatives thereof.

Preferred inhibitors for use in the methods described herein are soluble, CD2-binding LFA-3 polypeptides.

Soluble CD2 and LFA-3 Polypeptides

Soluble LEA-3 polypeptides or soluble CD2 polypeptides that inhibit the interaction of LFA-3 and CD2 are useful in the methods of the present invention. Soluble LFA-3 polypeptides, in particular soluble LFA-3/Ig fusions, are preferred.

As used herein, a "soluble CD2-binding LFA-3 polypeptide" is a polypeptide that includes at least the CD2-binding domain of LFA-3 and is incapable of anchoring itself in a membrane. Such soluble polypeptides include, for example, LFA-3 polypeptides that lack a sufficient portion of their membrane spanning domain to anchor the polypeptide or are modified such that the membrane spanning domain is nonfunctional. Soluble CD2-binding LFA-3 polypeptides include soluble fusion proteins that include at least the CD2-binding domain of LFA-3 fused to a heterologous polypeptide. In one embodiment, the heterologous polypeptide is an Fc region of an immunoglobulin (e.g., an IgG1 hinge region and CH2-CH3 domains) or a substantial portion thereof.

Soluble LFA-3 polypeptides may be derived from the transmembrane form of LFA-3, particularly the extracellular domain. Such polypeptides are described in U.S. Pat. No. 4,956,281 and U.S. Pat. No. 6,162,432, which are herein incorporated by reference. Preferred soluble LFA-3 polypeptides include polypeptides that include of residues 1-92 of SEQ ID NO:2, residues 1-80 of SEQ ID NO:2, residues 50-65 of SEQ ID NO:2 and resides 20-80 of SEQ ID NO:2, wherein SEQ ID NO:2 is shown in U.S. Pat. No. 6,162,432. A vector comprising a DNA sequence encoding SEQ ID NO:2 (i.e., SEQ ID NO:1) is deposited with the American Type Culture Collection, Manassas, Va. under Accession No. 75107, wherein of SEQ ID NO:1 and 2 are shown in U.S. Pat. No. 6,162,432.

Soluble LFA-3 polypeptides may also be derived from the PI-linked form of LFA-3, such as those described in PCT Patent Application Ser. No. WO 90/02181. A vector comprising a DNA sequence encoding PI-linked LFA-3 is deposited with the American Type Culture Collection, Manassas, Va. under Accession No. 68788. It is to be understood that the PI-linked form of LFA-3 and the transmembrane form of LFA-3 have identical amino acid sequences through the entire extracellular domain. Accordingly, the preferred PI-linked LFA-3 polypeptides are the same as for the transmembrane form of LFA-3.

The most preferred soluble CD-2 binding LFA-3 polypeptides for use in the present invention are LFA-3/Ig fusion proteins. One example of such a fusion protein is AMEVIVE® (alefacept).

AMEVIVE® (alefacept)

AMEVIVE is a fusion protein that includes the first extracellular domain of human LFA-3 (CD58) fused to an Fc portion of human IgG1. In particular, AMEVIVE includes the amino terminal 92 amino acids of mature LPA-3, the C-terminal 10 amino acids of a human IgG1 hinge region containing the two cysteine residues thought to participate in interchain disulfide bonding, and a substantial part of the $C_H2$ and $C_H3$ regions of a human $IgG_1$ heavy chain constant domain. The protein is a glycosylated, disulfide linked dimer with a molecular weight of about 112 kD under PAGE nonreducing conditions. The constant region of AMEVIVE has C-terminal variability which corresponds to a splice variant form of the full length fusion polypeptide.

A plasmid, pSAB152, encoding AMEVIVE is deposited with American Type Culture Collection, Manassas, Va., under the accession number ATCC 68720.

pMDR(92)Ig-3 is an example of an expression vector that can be used to produce AMEVIVE. pMDR(92)Ig-3 includes the following elements: (a) A segment of pBR322 containing the ColE1 origen and beta lactamase expression cassette (GenBank Accession No. J01749); (b) DHFR expression cassette consisting of: SV40 early promoter with the enhancer deleted (a portion of GenBank Accession No. J02400), murine DHFR cDNA (GenBank Accession No. L26316), SV40 poly A site and small t intron (portions of GenBank Accession No. J02400), and human gastrin transcription terminator sequence, 3'UTR (Sato et al. (1986) *Mol Cell Biol* 6:1032-1043); (c) an AMEVIVE expression cassette including, preferably in the following order: The SV40 early promoter/enhancer (GenBank Accession No. J02400), Adenovirus Major Late Promoter and tripartite leader, including a splice donor and intron sequence (a portion of GenBank Accession No. J01917), murine Ig heavy chain variable region intron sequence and splice acceptor (Kaufman and Sharp (1982) Mol Cell Biol. 2: 1304-1319, (optionally) cloning linkers, the first 92 amino acids of LFA-3 gene as isolated from a human tonsil cDNA library, fused in frame to a nucleic acid encoding the hinge CH2 and CH3 regions of a human IgG1 gene as isolated from a human fibroblastic genomic DNA library, cloning linkers (optionally), MIS 3' UT region including poly A site (GenBank Accession No. K03474), and SV40 polyA site and small t intron (GenBank Accession No. J02400); and a segment of pBR327 (GenBank Accession No. L08856).

Host cell lines that can be used to produce AMEVIVE can be derived from CHO-DUkX-B1 cells. In one embodiment, a DHFR(−) mutant of this cell line can be transfected with the vector pMDR(92)Ig-3, and DHFR(+) transformants can be cultured in selective medium (e.g., containing 25 nM of methotrexate (MTX)). Positive transformants can be subjected to increasing concentrations of MTX (e.g., 50 nM), and colonies producing high levels of AMEVIVE can then be selected.

Production of AMEVIVE can be carried out as follows: CHO host cells are thawed, scaled up to a culture of 2000 L, maintained in culture for 6-7 days with pH control and nutrient feed (at 48 hrs., 96 hrs., and 120 hrs.), after which conditioned medium is harvested through microfiltration. MTX is preferably present in the culture medium. AMEVIVE can be recovered from the conditioned medium by carrying out the following steps: (i) Protein A chromatography, (ii) ceramic hydroxyapatite chromatography, (iii) viral inactivation at low pH, (iv) hydrophobic interaction chromatography, (v) followed by concentration, diafiltration, viral filtration, and a second concentration step which yields fusion product.

Another way of producing AMEVIVE for use in the methods of this invention is described in co-pending, commonly assigned U.S. patent application Ser. No. 07/770,967. Generally, conditioned culture medium of COS7 or CHO cells transfected with pSAB152 was concentrated using an AMICON S1Y30 spiral cartridge system (AMICON, Danvers, Mass.) and subjected to Protein A-Sepharose 4B (Sigma, St. Louis, Mo.) chromatography. The bound proteins were eluted and subjected to Superose-12 (Pharmacia/LKB, Piscataway, N.J.) gel filtration chromatography.

Superose-12 fractions containing AMEVIVE with the least amount of contaminating proteins, as determined on SDS-PAGE gels and by Western blot analysis, (see, e.g., Towbin et al., *Proc. Natl. Acad. Sci. USA,* 74, pp. 4350-54 (1979); *Antibodies: A Laboratory Manual*, pp. 474-510 (Cold Spring Harbor Laboratory (1988)), were pooled and concentrated in a YM30 Centricon (AMICON). AMEVIVE was detected on Western blots using a rabbit anti-LFA-3 polyclonal antiserum, followed by detectably labeled goat anti-rabbit IgG. The purified AMEVIVE of COS7 or CHO cells was a dimer of two monomeric LFA-3-Ig fusion proteins, connected by disulfide bonds.

LFA-3-Ig fusion activity can be tested using the following bioassays: (1) a CD32/64 (Fc gamma RI/RII) U937 cell bridging assay, and (2) a CD16 (Fc gamma RIII) Jurkat cell bridging assay. Both assays test the ability of AMEVIVE to bridge CHO cells displaying cell surface CD2 to cells expressing Fc-gamma receptors. The latter assay, assay (2), involves culturing adherent CHO-CD2 cells to form a monolayer in 96-well plates; adding AMEVIVE controls and samples; adding fluorescently labeled Jurkat-CD16(+); and measuring fluorescence intensity.

Binding of LFA-3-Ig fusion to CD2 immobilized onto a substrate, e.g., a chip, can also be used to test the fusion proteins.

CD2 Polypeptides

Soluble CD2 polypeptides may be derived from full length CD2, particularly the extracellular domain. Such polypeptides may comprise all or part of the extracellular domain of CD2. Exemplary soluble CD2 polypeptides are described in PCT WO 90/08187, which is herein incorporated by reference.

Production of Soluble Polypeptides

The production of the soluble polypeptides useful in this invention may be achieved by a variety of methods known in the art. For example, the polypeptides may be derived from intact transmembrane LFA-3 or CD2 molecules or an intact PI-linked LFA-3 molecule by proteolysis using specific endopeptidases in combination with exopeptidases, Edman degradation, or both. The intact LFA-3 molecule or the intact CD2 molecule, in turn, may be purified from its natural source using conventional methods. Alternatively, the intact LFA-3 or CD2 may be produced by known recombinant DNA techniques using cDNAs (see, e.g., U.S. Pat. No. 4,956,281 to Wallner et al.; Aruffo and Seed, *Proc. Natl. Acad. Sci.,* 84, pp. 2941-45 (1987); Sayre et al., *Proc. Natl. Acad. Sci. USA,* 84, pp. 2941-45 (1987)).

Preferably, the soluble polypeptides useful in the present invention are produced directly, thus eliminating the need for an entire LFA-3 molecule or an entire CD2 molecule as a starting material. This may be achieved by conventional chemical synthesis techniques or by well-known recombinant DNA techniques wherein only those DNA sequences which encode the desired peptides are expressed in transformed hosts. For example, a gene which encodes the desired soluble LFA-3 polypeptide or soluble CD2 polypeptide may be synthesized by chemical means using an oligonucleotide synthesizer. Such oligonucleotides are designed based on the amino acid sequence of the desired soluble LFA-3 polypeptide or soluble CD2 polypeptide. Specific DNA sequences coding for the desired peptide also can be derived from the full length DNA sequence by isolation of specific restriction endonuclease fragments or by PCR synthesis of the specified region.

Standard methods may be applied to synthesize a gene encoding a soluble LFA-3 polypeptide or a soluble CD2 polypeptide that is useful in this invention. For example, the complete amino acid sequence may be used to construct a back-translated gene. A DNA oligomer containing a nucleotide sequence coding for a soluble LFA-3 polypeptide or a soluble CD2 polypeptide useful in this invention may be synthesized in a single step. Alternatively, several smaller oligonucleotides coding for portions of the desired polypeptide may be synthesized and then ligated. Preferably, a soluble LFA-3 polypeptide or a soluble CD2 polypeptide useful in this invention will be synthesized as several separate oligonucleotides which are subsequently linked together. The individual oligonucleotides typically contain 5' or 3' overhangs for complementary assembly.

Once assembled, preferred genes will be characterized by sequences that are recognized by restriction endonucleases (including unique restriction sites for direct assembly into a cloning or an expression vector), preferred codons taking into consideration the host expression system to be used, and a sequence which, when transcribed, produces a stable, efficiently translated mRNA. Proper assembly may be confirmed by nucleotide sequencing, restriction mapping, and expression of a biologically active polypeptide in a suitable host.

It will be appreciated by those of skill in the art that, due to the degeneracy of the genetic code, DNA molecules comprising many other nucleotide sequences will also be capable of encoding the soluble LFA-3 and CD2 polypeptides encoded by the specific DNA sequences described above. These degenerate sequences also code for polypeptides that are useful in this invention.

The DNA sequences may be expressed in unicellular hosts, or preferably in isolated mammalian host cells. As is well known in the art, in order to obtain high expression levels of a transfected gene in a host, the gene must be operatively linked to transcriptional and translational expression control sequences that are functional in the chosen expression host. Preferably, the expression control sequences, and the gene of interest, will be contained in an expression vector that further comprises a bacterial selection marker and origin of replication. If the expression host is a eukaryotic cell, the expression vector should further comprise an additional expression marker useful in the expression host.

The DNA sequences encoding the desired soluble polypeptides may or may not encode a signal sequence. If the expression host is prokaryotic, it generally is preferred that the DNA sequence not encode a signal sequence. If the expression host is eukaryotic, it generally is preferred that a signal sequence be encoded.

An amino terminal methionine may or may not be present on the expressed product. If the terminal methionine is not cleaved by the expression host, it may, if desired, be chemically removed by standard techniques.

A wide variety of expression host/vector combinations may be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from E. coli, including col E1, pCR1, pBR322, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2μ plasmid and derivatives thereof. Useful vectors for insect cells include pVL 941.

In addition, any of a wide variety of expression control sequences may be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast α-mating system and other sequences known to control the expression of genes of prokaryotic or eukaryotic cells or their viruses, and various combinations thereof.

A wide variety of host cells are useful. Host cells can be a unicellular organism, or can be obtained from a multicellular organism, e.g., isolated cells from a multicellular host. These hosts may include well known eukaryotic and prokaryotic hosts, such as strains of E. coli, Pseudomonas, Bacillus, Streptomyces, fungi, yeast, insect cells such as Spodoptera frugiperda (SF9), animal cells such as CHO and mouse cells, African green monkey cells such as COS 1, COS 7, BSC 1, BSC 40, and BMT 10, and human cells, as well as plant cells in tissue culture. For animal cell expression, CHO cells and COS 7 cells are preferred.

It should be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered.

In selecting an expression control sequence, a variety of factors should also be considered. These include, for example, the relative strength of the sequence, its controllability, and its compatibility with the DNA sequences discussed herein, particularly as regards potential secondary structures. Unicellular hosts should be selected by consideration of their compatibility with the chosen vector, the toxicity of the product coded for by the DNA sequences, their secretion characteristics, their ability to fold the soluble polypeptides correctly, their fermentation or culture requirements, and the ease of purification of the products coded for by the DNA sequences.

Within these parameters, one of skill in the art may select various vector/expression control sequence/host combinations that will express the desired DNA sequences on fermentation or in large scale animal culture, for example with CHO cells or COS 7 cells.

The soluble LFA-3 and CD2 polypeptides may be isolated from the fermentation or cell culture and purified using any of a variety of conventional methods. One of skill in the art may select the most appropriate isolation and purification techniques.

While recombinant DNA techniques are the preferred method of producing useful soluble CD2 polypeptides or soluble LFA-3 polypeptides having a sequence of more than 20 amino acids, shorter CD2 or LFA-3 polypeptides having less than about 20 amino acids are preferably produced by conventional chemical synthesis techniques. Synthetically produced polypeptides useful in this invention can advantageously be produced in extremely high yields and can be easily purified.

Preferably, such soluble CD2 polypeptides or soluble LFA-3 polypeptides are synthesized by solution phase or solid phase polypeptide synthesis and, optionally, digested with carboxypeptidase (to remove C-terminal amino acids) or degraded by manual Edman degradation (to remove N-terminal amino acids). The use of solution phase synthesis advantageously allows for the direct addition of certain derivatized amino acids to the growing polypeptide chain, such as the O-sulfate ester of tyrosine. This obviates the need for a subsequent derivatization step to modify any residue of the polypeptides useful in this invention.

Proper folding of the polypeptides may be achieved under oxidative conditions which favor disulfide bridge formation as described by Kent, "Chemical Synthesis of Polypeptides and Proteins", *Ann. Rev. Biochem.*, 57, pp. 957-89 (1988). Polypeptides produced in this way may then be purified by separation techniques widely known in the art.

Anti-LFA-3 And Anti-CD2 Antibody Homologs

As used herein, an "antibody homolog" is a protein comprising one or more polypeptides selected from immunoglobulin light chains, immunoglobulin heavy chains and antigen-binding fragments thereof which are capable of binding to an antigen. The component polypeptides of an antibody homolog composed of more than one polypeptide may optionally be disulfide-bound or otherwise covalently crosslinked. Accordingly, antibody homologs include intact immunoglobulins of types IgA, IgG, IgE, IgD, IgM (as well as subtypes thereof), wherein the light chains of the immunoglobulin may be of types kappa or lambda. Antibody homologs also include portions of intact immunoglobulins that retain antigen-binding specificity, for example, Fab fragments, Fab' fragments, F(ab')$_2$ fragments, F(v) fragments, heavy chain monomers or dimers, light chain monomers or dimers, dimers consisting of one heavy and one light chain, and the like. The term includes recombinant antiboides, chimeric, CDR-grafted and humanized antibodies, or other antibodies modified to be less immunogenic in a human.

As used herein, a "humanized recombinant or humanized antibody homolog" is an antibody homolog, produced by recombinant DNA technology, in which some or all of the amino acids of a human immunoglobulin light or heavy chain that are required for antigen binding have been substituted for the corresponding amino acids from a nonhuman mammalian immunoglobulin light or heavy chain.

As used herein, a "chimeric recombinant antibody homolog" is an antibody homolog, produced by recombinant DNA technology, in which all or part of the hinge and constant regions of an immunoglobulin light chain, heavy chain, or both, have been substituted for the corresponding regions from another immunoglobulin light chain or heavy chain.

Many types of anti-LFA-3 or anti-CD2 antibody homologs are useful in the methods of this invention. These include monospecific (e.g., monoclonal) antibodies, recombinant antibodies, chimeric recombinant antibodies, humanized recombinant antibodies, as well as antigen-binding portions of the foregoing.

Among the anti-LFA-3 antibody homologs, it is preferable to use monoclonal anti-LFA-3 antibodies. It is more preferable to use a monoclonal anti-LFA-3 antibody produced by a hybridoma selected from the group of hybridomas having Accession Nos. ATCC HB 10693 (1E6), ATCC HB 10694 (HC-1B11), ATCC HB 10695 (7A6), and ATCC HB 10696 (8B8), or the monoclonal antibody known as TS2/9 (Sanchez-Madrid et al., "Three Distinct Antigens Associated with Human T-Lymphocyte-Mediated Cytolysis: LFA-1, LFA-2 and LFA-3", Proc. Natl. Acad. Sci. USA, 79, pp. 7489-93 (1982)). Most preferably, the monoclonal anti-LFA-3 antibody is produced by a hybridoma selected from the group of hybridomas having Accession Nos. ATCC HB 10695 (7A6) and ATCC HB 10693 (1E6).

Among the anti-CD2 antibody homologs, it is preferable to use monoclonal anti-CD2 antibodies, such as the anti-CD2 monoclonal antibodies known as the $T11_1$ epitope antibodies, including TS2/18 (Sanchez-Madrid et al., "Three Distinct Antigens Associated with Human T-Lymphocyte-Mediated Cytolysis: LFA-1, LFA-2 and LFA-3", Proc. Natl. Acad. Sci. USA, 79, pp. 7489-93 (1982)).

The technology for producing monoclonal antibodies is well known. See generally, Harlow, E. and Lane, D. (1988) *Antibodies: A Laboratory Manual*, Cold Spring Harbor Laboratory Press, Cold Spring Harbor, N.Y.; Kohler et al., *Nature*, "Continuous Cultures of Fused Cells Secreting Antibody of Predefined Specificity", 256, pp. 495-97 (1975). Useful immunogens for the purpose of this invention include CD2- or LFA-3-bearing cells, as well as cell free preparations containing LFA-3, CD2 or counter receptor-binding fragments thereof (e.g., CD2 fragments that bind to LFA-3 or LFA-3 fragments that bind to CD2).

Immunization may be accomplished using standard procedures. The unit dose and immunization regimen depend on the species of mammal immunized, its immune status, the body weight of the mammal, etc. Typically, the immunized mammals are bled and the serum from each blood sample is assayed for particular antibodies using appropriate screening assays. For example, useful anti-LFA-3 or anti-CD2 antibodies may be identified by testing the ability of the immune serum to block sheep red blood cell rosetting of Jurkat cells, which results from the presence of LFA-3 and CD2 on the respective surfaces of these cells. The lymphocytes used in the production of hybridoma cells typically are isolated from immunized mammals whose sera have already tested positive for the presence of the desired antibodies using such screening assays.

Anti-CD2 and anti-LFA-3 antibody homologs useful in the present invention may also be recombinant antibodies produced by host cells transformed with DNA encoding immunoglobulin light and heavy chains of a desired antibody. Recombinant antibodies may be produced by well known genetic engineering techniques. See, e.g., U.S. Pat. No. 4,816, 397, which is incorporated herein by reference. For example, recombinant antibodies may be produced by cloning cDNA or genomic DNA encoding the immunoglobulin light and heavy chains of the desired antibody from a hybridoma cell that produces an antibody homolog useful in this invention. The cDNA or genomic DNA encoding those polypeptides is then inserted into expression vectors so that both genes are operatively linked to their own transcriptional and translational expression control sequences. The expression vector and expression control sequences are chosen to be compatible with the expression host cell used. Typically, both genes are inserted into the same expression vector.

Prokaryotic or eukaryotic host cells may be used. Expression in eukaryotic host cells is preferred because such cells are more likely than prokaryotic cells to assemble and secrete a properly folded and immunologically active antibody. It is possible that the host cells will produce portions of intact antibodies, such as light chain dimers or heavy chain dimers, which also are antibody homologs according to the present invention.

It will be understood that variations on the above procedure are useful in the present invention. For example, it may be desired to transform a host cell with DNA encoding either the light chain or the heavy chain (but not both) of an antibody homolog. Recombinant DNA technology may also be used to remove some or all of the DNA encoding either or both of the light and heavy chains that is not necessary for CD2 or LFA-3 counter receptor binding. The molecules expressed from such truncated DNA molecules are useful in the methods of this invention. In addition, bifunctional antibodies may be produced in which one heavy and one light chain are anti-CD2 or anti-LFA-3 antibody homologs and the other heavy and light chain are specific for an antigen other than CD2 or LFA-3, or another epitope of CD2 or LFA-3.

Chimeric recombinant anti-LFA-3 or anti-CD2 antibody homologs may be produced by transforming a host cell with a suitable expression vector comprising DNA encoding the desired immunoglobulin light and heavy chains in which all or some of the DNA encoding the hinge and constant regions of the heavy and/or the light chain have been substituted with DNA from the corresponding region of an immunoglobulin light or heavy chain of a different species. When the original recombinant antibody is nonhuman, and the inhibitor is to be administered to a human, substitution of corresponding human sequences is preferred. An exemplary chimeric recombinant antibody has mouse variable regions and human hinge and constant regions. See generally, U.S. Pat. No. 4,816,397; Morrison et al., "Chimeric Human Antibody Molecules: Mouse Antigen-Binding Domains With Human Constant Region Domains", *Proc. Natl. Acad. Sci. USA*, 81, pp. 6851-55 (1984); Robinson et al., International Patent Publication PCT/US86/02269; Akira, et al., European Patent Application 184,187; Taniguchi, M., European Patent Application 171,496; Neuberger et al., International Application WO 86/01533; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

Humanized recombinant anti-LFA-3 or anti-CD2 antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an anti-LFA-3 or anti-CD2 antibody. Nucleic acids encoding the humanized antibody, or fragment thereof, can then be cloned into an appropriate expression vector.

Humanized or CDR-grafted antibody molecules or immunoglobulins can be produced by CDR-grafting or CDR substitution, wherein one, two, or all CDR's of an immunoglobulin chain can be replaced. See e.g., U.S. Pat. No. 5,225,539; Jones et al. 1986 Nature 321:552-525; Verhoeyan et al. 1988 Science 239:1534; Beidler et al. 1988 J. Immunol. 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference. All of the CDR's of a particular human antibody may be replaced with at least a portion of a non-human CDR or only some of the CDR's may be replaced with non-human CDR's. It is only necessary to replace the number of CDR's required for binding of the humanized antibody to a predetermined antigen, e.g., LFA-3 or CD2.

Also within the scope of the invention are humanized antibodies, including immunoglobulins, in which specific amino acids have been substituted, deleted or added. In particular, preferred humanized antibodies have amino acid substitutions in the framework region, such as to improve binding to the antigen. For example, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the contents of which are hereby incorporated by reference. Other techniques for humanizing immunoglobulin chains, including antibodies, are described in Padlan et al. EP 519596 A1, published on Dec. 23, 1992.

Human monoclonal antibodies (mAbs) directed against human LFA-3 or CD2 can be generated using transgenic mice carrying the complete human immune system rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326).

Monoclonal antibodies can also be generated by other methods known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. 1989 PNAS 86:5728; Huse et al. 1989 Science 246:1275; and Orlandi et al. 1989 PNAS 86:3833). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and PCR (Larrick et al.,1991, Biotechniques 11:152-156; Larrick et al., 1991, Methods: Companion to Methods in Enzymology 2:106-110).

Examples of methods and reagents particularly amenable for use in generating a variegated antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J 12:725-734; Hawkins et al. (1992) J Mol Biol 226: 889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982. Kits for generating phage display libraries are commercially available (e.g., the Pharmacia Recombinant Phage Antibody System, catalog no. 27-9400-01; and the Stratagene SurfZAP™ phage display kit, catalog no. 240612).

In certain embodiments, the V region domains of heavy and light chains can be expressed on the same polypeptide, joined by a flexible linker to form a single-chain Pv fragment, and the scFV gene subsequently cloned into the desired expression vector or phage genome. As generally described in McCafferty et al., Nature (1990) 348:552-554, complete VH and VL domains of an antibody, joined by a flexible (Gly4-Ser)3 linker can be used to produce a single chain antibody which can render the display package separable based on antigen affinity. Isolated scFV antibodies immunoreactive with the antigen can subsequently be formulated into a pharmaceutical preparation for use in the subject method.

Specific antibodies with high affinities for a surface protein can be made according to methods known to those in the art, e.g, methods involving screening of libraries (Ladner, R. C., et al., U.S. Pat. No. 5,233,409; Ladner, R. C., et al., U.S. Pat. No. 5,403,484). Further, the methods of these libraries can be used in screens to obtain binding determinants that, are mimetics of the structural determinants of antibodies. See for example Bajorath, J. and S. Sheriff, 1996, Proteins: Struct., Funct., and Genet. 24 (2), 152-157; Webster, D. M. and A. R. Rees, 1995, "Molecular modeling of antibody-combining sites," in S. Paul, Ed., Methods in Molecular Biol. 51, Antibody Engineering Protocols, Humana Press, Totowa, N.J., pp 17-49; and Johnson, G., Wu, T. T. and E. A. Kabat, 1995, "Seqhunt: A program to screen aligned nucleotide and amino acid sequences," in Methods in Molecular Biol. 51, op. cit., pp 1-15.

Anti-CD2 and anti-LFA-3 antibody homologs that are not intact antibodies are also useful in this invention. Such homologs may be derived from any of the antibody homologs described above. For example, antigen-binding fragments, as well as full-length monomeric, dimeric or trimeric polypeptides derived from the above-described antibodies are themselves useful. Useful antibody homologs of this type include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Anti-LFA-3 heavy chains are preferred anti-LFA-3 antibody fragments.

Antibody fragments may also be produced by chemical methods, e.g., by cleaving an intact antibody with a protease, such as pepsin or papain, and optionally treating the cleaved product with a reducing agent. Alternatively, useful fragments may be produced by using host cells transformed with truncated heavy and/or light chain genes. Heavy and light chain monomers may be produced by treating an intact antibody with a reducing agent, such as dithiothreitol, followed by purification to separate the chains. Heavy and light chain monomers may also be produced by host cells transformed with DNA encoding either the desired heavy chain or light chain, but not both. See, e.g., Ward et al., "Binding Activities of a Repertoire of Single immunoglobulin Variable Domains Secreted from *Escherichia coli*", *Nature*, 341, pp. 544-46 (1989); Sastry et al., "Cloning of the Immunological Repertoire in *Escherichia coli* for Generation of Monoclonal Catalytic Antibodies: Construction of a Heavy Chain Variable Region-Specific cDNA Library", *Proc. Natl. Acad. Sci. USA*, 86, pp. 5728-32 (1989).

LFA-3 And CD-2 Mimetic or Small Molecule Agents

Also useful in the methods of this invention are LFA-3 and CD2 mimetic agents. These agents which may be peptides, semi-peptidic compounds or non-peptidic compounds (e.g., small organic molecules), are inhibitors of the CD2:LFA-3 interaction. A preferred CD2 and LFA-3 mimetic agents will inhibit the CD2:LFA-3 interaction at least as well as anti-LFA-3 monoclonal antibody 7A6 or anti-CD2 monoclonal antibody TS2/18 (described supra).

In preferred embodiments, the test agent is a member of a combinatorial library, e.g., a peptide or organic combinatorial library, or a natural product library. In a preferred embodiment, the plurality of test compounds, e.g., library members, includes at least 10, $10^2$, $10^3$, $10^4$, $10^5$, $10^6$, $10^7$, or $10^8$ compounds. In a preferred embodiment, the plurality of test compounds, e.g., library members, share a structural or functional characteristic.

In one embodiment, the invention provides libraries of LFA-3 and/or CD2 inhibitors. The synthesis of combinatorial libraries is well known in the art and has been reviewed (see, e.g., E. M. Gordon et al., *J. Med. Chem.* (1994) 37:1385-1401; DeWitt, S. H.; Czarnik, A. W. *Acc. Chem. Res.* (1996) 29:114; Armstrong, R. W.; Combs, A. P.; Tempest, P. A.; Brown, S. D.; Keating, T. A. *Acc. Chem. Res.* (1996) 29:123; Ellman, J. A. *Acc. Chem. Res.* (1996) 29:132; Gordon, E. M.; Gallop, M. A.; Patel, D. V. *Acc. Chem. Res.* (1996) 29:144; Lowe, G. *Chem. Soc. Rev.* (1995) 309, Blondelle et al. *Trends Anal. Chem.* (1995) 14:83; Chen et al. *J. Am. Chem. Soc.* (1994) 116:2661; U.S. Pat. Nos. 5,359,115, 5,362,899, and 5,288,514; PCT Publication Nos. WO92/10092, WO93/09668, WO91/07087, WO93/20242, WO94/08051).

Libraries of compounds of the invention can be prepared according to a variety of methods, some of which are known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., M. Bodansky "Principles of Peptide Synthesis", 2nd edition, Springer-Verlag, Berlin (1993)). To each aliquot of beads is added a solution of a different activated amino acid, and the reactions are allow to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen binding site. It will be appreciated that a wide variety of peptidic, peptidomimetic, or non-peptidic compounds can be readily generated in this way.

The "split-pool" strategy results in a library of peptides, e.g., inhibitors, which can be used to prepare a library of test compounds of the invention. In another illustrative synthesis, a "diversomer library" is created by the method of Hobbs DeWitt et al. (*Proc. Natl. Acad. Sci. U.S.A.* 90:6909 (1993)). Other synthesis methods, including the "tea-bag" technique of Houghten (see, e.g., Houghten et al., *Nature* 354:84-86 (1991)) can also be used to synthesize libraries of compounds according to the subject invention.

Libraries of compounds can be screened to determine whether any members of the library have a desired activity, and, if so, to identify the active species. Methods of screening combinatorial libraries have been described (see, e.g., Gordon et al., *J Med. Chem., supra)*. Soluble compound libraries can be screened by affinity chromatography with an appropriate receptor to isolate ligands for the receptor, followed by identification of the isolated ligands by conventional techniques (e.g., mass spectrometry, NMR, and the like). Imobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening the libraries of the invention are described below.

In one embodiment, compounds of the invention can be screened for the ability to interact with a CD2 or LFA-3 polypeptide by assaying the activity of each compound to bind directly to the polypeptide or to inhibit a CD2:LFA-3 interaction, e.g., by incubating the test compound with a CD2 or LFA-3 polypeptide and a lysate, e.g., a T or APC cell lysate, e.g., in one well of a multiwell plate, such as a standard 96-well microtiter plate. In this embodiment, the activity of each individual compound can be determined. A well or wells having no test compound can be used as a control. After incubation, the activity of each test compound can be determined by assaying each well. Thus, the activities of a plurality of test compounds can be determined in parallel.

In still another embodiment, large numbers of test compounds can be simultaneously tested for binding activity. For example, test compounds can be synthesized on solid resin beads in a "one bead-one compound" synthesis; the compounds can be immobilized on the resin support through a photolabile linker. A plurality of beads (e.g., as many as 100,000 beads or more) can then be combined with yeast cells and sprayed into a plurality of "nano-droplets", in which each droplet includes a single bead (and, therefore, a single test compound). Exposure of the nano-droplets to UV light then results in cleavage of the compounds from the beads. It will be appreciated that this assay format allows the screening of large libraries of test compounds in a rapid format.

Combinatorial libraries of compounds can be synthesized with "tags" to encode the identity of each member of the library (see, e.g., W. C. Still et al., U.S. Pat. No. 5,565,324 and PCT Publication Nos. WO 94/08051 and WO 95/28640). In general, this method features the use of inert, but readily detectable, tags, that are attached to the solid support or to the compounds. When an active compound is detected (e.g., by one of the techniques described above), the identity of the compound is determined by identification of the unique accompanying tag. This tagging method permits the synthesis of large libraries of compounds which can be identified at very low levels. Such a tagging scheme can be useful, e.g., in the "nano-droplet" screening assay described above, to identify compounds released from the beads.

In preferred embodiments, the libraries of compounds of the invention contain at least 30 compounds, more preferably at least 100 compounds, and still more preferably at least 500 compounds. In preferred embodiments, the libraries of compounds of the invention contain fewer than $10^9$ compounds, more preferably fewer than $10^8$ compounds, and still more preferably fewer than $10^7$ compounds.

Derivatized Inhibitors

Also useful in the methods of this invention are derivatized inhibitors of the CD2:LFA-3 interaction in which, for example, any of the antibody homologs, soluble CD2 and LFA-3 polypeptides, or CD2 and LFA-3 mimetic agents described herein are functionally linked (by chemical coupling, genetic fusion or otherwise) to one or more members independently selected from the group consisting of anti-LFA-3 and anti-CD2 antibody homologs, soluble LFA-3 and CD2 polypeptides, CD2 and LFA-3 mimetic agents, cytotoxic agents and pharmaceutical agents.

One type of derivatized inhibitor is produced by crosslinking two or more inhibitors (of the same type or of different types). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Another possibility for cross-linking takes advantage of the PI linkage signal sequence in PI-linked LFA-3, or fragments thereof. Specifically, DNA encoding the PI-linkage signal sequence is ligated downstream of DNA encoding a desired polypeptide, preferably a soluble LFA-3 polypeptide. If this construct is expressed in an appropriate eukaryotic cell, the cell will recognize the PI linkage signal sequence and will covalently link PI to the polypeptide. The hydrophobic property of the PI may then be exploited to form micellar aggregates of the polypeptides.

Also useful are inhibitors linked to one or more cytotoxic or pharmaceutical agents. Useful pharmaceutical agents include biologically active peptides, polypeptides and proteins, such as antibody homologs specific for a human polypeptide other than CD2 or LFA-3, or portions thereof. Useful pharmaceutical agents and cytotoxic agents also include daunorubicin, *Pseudomonas* exotoxin A, interferon, and nitrogen mustard.

Preferred inhibitors derivatized with a pharmaceutical agent include recombinantly-produced polypeptides in which a soluble LFA-3 polypeptide, soluble CD2 polypeptide, or a peptidyl CD2 or peptidyl LFA-3 mimetic agent is fused to all or part of an immunoglobulin heavy chain hinge region and all or part of a heavy chain constant region. Preferred polypeptides for preparing such fusion proteins are soluble LFA-3 polypeptides. Most preferred are fusion proteins containing amino acid 1-92 of mature LFA-3 fused to a portion of a human $IgG_1$ hinge region (including the C-terminal ten amino acids of the hinge region containing two cysteine residues thought to participate in interchain disulfide bonding) and the $C_H2$ and $C_H3$ regions of an $IgG_1$ heavy chain constant domain. Such fusion proteins are expected to exhibit prolonged serum half-lives and enable inhibitor dimerization.

The utility in the methods of this invention of specific soluble CD2 polypeptides, soluble LFA-3 polypeptides, anti-LFA-3 antibody homologs, anti-CD2 antibody homologs or CD2 and LFA-3 mimetic agents may easily be determined by assaying their ability to inhibit the LFA-3/CD2 interaction. This ability may be assayed, for example, using a simple cell binding assay that permits visual (under magnification) evaluation of the ability of the putative inhibitor to inhibit the interaction between LFA-3 and CD2 on cells bearing these molecules. Jurkat cells are preferred as the CD2+ substrate and sheep red blood cells or human JY cells are preferred as the LFA-3+ substrate. The binding characteristics of soluble polypeptides, antibody homologs and mimetic agents useful in this invention may be assayed in several known ways, such as by radiolabeling the antibody homolog, polypeptide or agent (e.g., $^{35}S$ or $^{125}I$) and then contacting the labeled polypeptide, mimetic agent or antibody homolog with $CD2^+$ of $LFA-3^+$ cells, as appropriate. Binding characteristics may also be assayed using an appropriate enzymatically labelled secondary antibody. Rosetting competition assays such as those described by Seed et al. (*Proc. Natl. Acad. Sci. USA*, 84, pp. 3365-69 (1987)) may also be used.

Combination Therapy

The agents, e.g., soluble, CD2-binding LFA-3 polypeptides, may be used in combination with other therapies, e.g., other agents. The other agent(s) are referred to herein as "second agent(s)" or "additional agents" and include one or more of: a protease inhibitor, eg., Agenerase (amprenavir), Viracept (nelfinavir), Crixivan (indinavir), Reyataz (atazanavir; BMS-232632), Norvir (ritonavir), Lexiva (Fosamprenavir), Kaletra (lopinavir), Invirase (saquinavir), Fortovase (saquinavir); a reverse transcriptase inhibitor, e.g., Retrovir, AZT (zidovudine), Rescriptor (delavirdine), Sustiva (efavirenz), Ziagen (abacavir), Zerit (d4t/stavudine), Viread (tenofovir disoproxil fumarate), Viramune (nevirapine), Videx (ddI/didanosine); Emtriva [emtricitabine CITC)], Fuzeon (enfuvirtide), or combinations of any of the foregoing, e.g., HAART. Such combination therapy may advantageously utilize lower dosages of the therapeutic or prophylactic agents.

Administered "in combination", as used herein, means that two, three, or more, different treatments are delivered to the subject during the course of the subject's affliction with the disorder, e.g., the two or more treatments are delivered after the subject has been diagnosed with the infection and before the infection is in remission, or has been cured or eliminated. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. E.g., the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder, e.g., reduction in memory T cell level or activity, or reduction in viral load, is greater than what would be observed with one treatment delivered in the absence of the other. The effect of the two treatments can be partially additive, wholly additive, or greater than additive. The delivery can be such that an effect of the first treatment delivered is still detectable when the second is delivered, e.g., when the CD2- or LFA-3 binding agent is delivered first, a reduction in T cell level or activity is still detectable when second agent is delivered. In a preferred embodiment, a delivery of the first treatment and a delivery of the second treatment occur within 1, 2, 5, 10, 15, or 30 days of one another.

In a preferred embodiment, the CD2-binding agent (e.g., LFA-3/Ig fusion), the second agent (or both) or a pharmaceutical composition containing the same is administered systemically, e.g., intravenously, intramuscularly, subcutaneously, intra-articularly, transdermally, intrathecally, periostally, intratumorally, intralesionally, perilesionally by infusion (e.g., using an infusion device), orally, topically or by inhalation. Preferably, the CD2-binding agent is administered intramuscularly or intravenously. In other embodiment, the CD2-binding agent is administered locally, e.g., topically or by needleless injection, to an affected area.

The parenteral administration of the CD2-binding agent (e.g., LFA-3/Ig fusion), the second agent (or both) or a pharmaceutical composition containing the same can be effected using a needle or a needleless syringe by procedures known in the art. Examples of needleless syringe systems and modes of administration are described in U.S. Pat. No. 6,132,395, U.S. Pat. No. 6,096,002, U.S. Pat. No. 5,993,412, U.S. Pat. No. 5,893,397, U.S. Pat. No. 5,520,639, U.S. Pat. No. 5,503,627, U.S. Pat. No. 5,399,163, U.S. Pat. No. 5,383,851, U.S. Pat. No. 5,312,577, U.S. Pat. No. 5,312,335, the contents of all of which are hereby incorporated by reference.

Pharmaceutical Compositions

Preferably, an effective amount of the CD2:LFA3 inhibitor (e.g., a soluble, CD2-binding LFA-3 polypeptide described herein) is administered. By "effective amount" is meant an amount capable of lessening the spread or severity of the conditions described herein. In therapeutic embodiments, an effective amount of the agent refers to an amount of an agent which is effective at inhibiting, reducing, or ameliorating the disorder (e.g., reducing the viral load or increasing CD4 cell count for an HIV+ patient), or in prolonging the survival of the patient with the disorder beyond that expected in the absence of such treatment. An effective amount does not necessarily indicate a total elimination of the virus. In prophylactic embodiments, an effective amount of a CD2- or LFA-3 binding agent described herein refers to an amount of an agent which is effective in preventing or delaying the occurrence of the onset or recurrence of the disorder (e.g., AIDS) associated with the virus.

It will be apparent to those of skill in the art that the effective amount of agent will depend, inter alia, upon the disorder treated (e.g., HIV/AIDS vs. HCV), administration schedule, the unit dose administered, whether the agent is administered in combination with other therapeutic agents, the immune status and health of the patient, the therapeutic or prophylactic activity of the particular agent administered and the serum half-life. Depending on the disorder to be treated the agent may be packaged differently.

Preferably, a soluble, CD2-binding LFA-3 polypeptide (e.g., LFA3TIP) is administered at a dose between about 0.001 and about 50 mg of the agent per kg body weight, more preferably, between about 0.01 and about 10 mg of the agent per kg body weight, most preferably between about 0.1 and about 4 mg of the agent per kg body weight. In preferred embodiment, the soluble, CD2-binding LFA-3 polypeptide is administered at a unit dosage ranging from 2 to 15 mg when administered by IV route (for example, 7.5 mg IV bolus) and a dosage ranging from 2 to 30 mg when administered by IM route (for example, 15 mg IM injection). IM and IV administration are preferred.

Unit doses are typically administered until an effect is observed. The effect may be measured by a variety of methods, including, in vitro T cell activity assays and clearing or improvement of affected skin areas, or improvement in other affected body areas as may be relevant to the particular disorder. Preferably, the unit dose is administered at regular intervals during a treatment cycle, such as once a week. More preferably, it is administered at regular intervals, e.g., at weekly intervals for an administration period of several weeks, e.g., twelve weeks. More frequent administrations, e.g., two or three times per week are also envisioned and may be adapted if the subject's disorder is severe or if urgent intervention is indicated. Less frequent administrations, e.g., once or twice per month, are also envisioned and may be adopted if the subject responds well to therapy such that maintenance dosing is appropriate. It will be recognized, however, that lower or higher dosages and other administration schedules may be employed during any one particular cycle of administration.

The agent, e.g., CD2-binding LFA-3 polypeptide (e.g., AMEVIVE) is also preferably administered in a composition including a pharmaceutically acceptable carrier. By "pharmaceutically acceptable carrier" is meant a carrier that does not cause an allergic reaction or other untoward effect in patients to whom it is administered.

Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the agent.

Formulations, e.g., pharmaceutical formulations, of the CD2-binding agent(s) can be prepared in aqueous or non-aqueous, e.g., lyophilized, forms. Preferred pharmaceutical formulations are suitable for injection. An example of an aqueous formulation encompassed by the present invention includes phosphate buffered saline (PBS) frozen liquid formulation. An example of a lyophilized formulation includes one or more of: citrate, glycine and sucrose. For example, a preferred lyophilized formulation includes 1 to 5% sucrose, preferably 2.5% sucrose, and 0.5% to 2% glycine, preferably 1% glycine, in sodium citrate-citric buffer (at least 10 mM, preferably 25 mM) buffered to a pH of at least about 4, preferably, 5, more preferably 6 (or even more preferably, 6.8).

The second agent may be administered in a single dosage form with the CD2-binding agent(s) (i.e., as part of the same pharmaceutical composition), a multiple dosage form, separately from the CD2-binding agent(s) but concurrently, or a multiple dosage form wherein the two components are administered separately and sequentially. Alternatively, the CD2-binding agent and the other active agent may be in the form of a single conjugated molecule. Conjugation of the two components may be achieved by standard cross-linking techniques well known in the art. A single molecule may also take the form of a recombinant fusion protein. In addition, a pharmaceutical composition useful in the present invention may be used in combination with other therapies such as anti-retroviral drugs (e.g., protease inhibitors). Such combination therapies may advantageously utilize lower dosages of the therapeutic or prophylactic agents.

The CD2-binding agent, or pharmaceutical composition, may be in a variety of forms. These include, for example, solid, semi-solid and liquid dosage forms, such as tablets, pills, powders, liquid solutions, dispersions or suspensions, liposomes, suppositories, injectable, infusible, and topical preparations. The preferred form depends on the intended mode of administration and therapeutic application. The preferred forms are injectable or infusible solutions.

We claim:

1. A method of treating a subject infected with a pathogenic virus, the method comprising administering alefacept (SEQ ID NO:4) to the subject, wherein the pathogenic virus is selected from the group consisting of hepatitis C (HCV), hepatitis B (HBV), hepatitis D (HDV), human T lymphotropic virus-1(HLTV-1), human T lymphotrophic virus-2 (HLTV-2), Epstein-Barr virus (EBV), cytomegalovirus (CMV), herpes simplex type 1 (HSV-1), herpes simplex type 2 (HSV-2), herpes zoster virus (HZV), herpes virus type 6 (HHV-6), herpes virus type 7 (HHV-7), and papillomavirus.

* * * * *

UNITED STATES PATENT AND TRADEMARK OFFICE
CERTIFICATE OF CORRECTION

| | |
|---|---|
| PATENT NO. | : 7,662,921 B2 |
| APPLICATION NO. | : 11/578391 |
| DATED | : February 16, 2010 |
| INVENTOR(S) | : Burt Adelman et al. |

It is certified that error appears in the above-identified patent and that said Letters Patent is hereby corrected as shown below:

In Column 1, at line 28, "N. Engl. S. Med." should read --N. Engl. J. Med.--

In Column 1, at line 52, "AMVIVE®" should read --AMEVIVE®--

In Column 1, at line 53, "AMEEVIVE" should read --AMEVIVE--

In Column 12, at line 38, "Pv fragment" should read --Fv fragment--

In Column 16, at line 66, "CITC)" should read --(FTC)--

Signed and Sealed this
Twenty-second Day of March, 2011

David J. Kappos
*Director of the United States Patent and Trademark Office*